(12) United States Patent
Clark et al.

(10) Patent No.: US 9,121,801 B2
(45) Date of Patent: Sep. 1, 2015

(54) METHODS AND DEVICES FOR CELLULAR ANALYSIS

(75) Inventors: Douglas P. Clark, Baltimore, MD (US);
Adam Schayowitz, Bethesda, MD (US);
Kathleen M. Murphy, Baltimore, MD (US); Scott Diamond, Bala Cynwyd, PA (US)

(73) Assignee: BioMarker Strategies, LLC, Rockville, MD (US)

( * ) Notice: Subject to any disclaimer, the term of this patent is extended or adjusted under 35 U.S.C. 154(b) by 795 days.

(21) Appl. No.: 12/258,251

(22) Filed: Oct. 24, 2008

(65) Prior Publication Data
US 2009/0162853 A1    Jun. 25, 2009

Related U.S. Application Data

(60) Provisional application No. 61/099,059, filed on Sep. 22, 2008, provisional application No. 60/982,279, filed on Oct. 24, 2007.

(51) Int. Cl.
| | | |
|---|---|---|
| *G01N 1/28* | (2006.01) | |
| *G01N 33/574* | (2006.01) | |
| *G01N 1/30* | (2006.01) | |
| *G01N 15/14* | (2006.01) | |
| *G01N 35/10* | (2006.01) | |

(52) U.S. Cl.
CPC .... *G01N 15/1475* (2013.01); *G01N 2035/1032* (2013.01)

(58) Field of Classification Search
None
See application file for complete search history.

(56) References Cited

U.S. PATENT DOCUMENTS

| | | |
|---|---|---|
| 3,941,317 A | 3/1976 | Kanor |
| 4,350,768 A | 9/1982 | Tihon et al. |
| 2004/0014097 A1 | 1/2004 | McGlennen et al. |
| 2005/0233309 A1 | 10/2005 | Hankins |

FOREIGN PATENT DOCUMENTS

| | | |
|---|---|---|
| EP | 0 590 504 A | 4/1994 |
| WO | WO-93/24607 A | 12/1993 |
| WO | 03/027236 A2 | 4/2003 |
| WO | 2007/075440 A2 | 7/2007 |

OTHER PUBLICATIONS

Wiernik et al. "Neoplastic Diseases of the Blood," Fourth Edition, Cambridge University Press, 2003, p. 1055.*
Polanski et al. "A List of Candidate Cancer Biomarkers for Targeted Proteomics," Biomarker Insights, 2006, vol. 2, pp. 1-48.*
Deepanwita Das, "Red Bllod Cell Stabilization: Effect on Hydroxyethyl starch on RBC Viability, functionality and Oxidative state during Freeze Thaw Conditions," eThesis, 2009, title page.*
International Search Report for PCT/US2008/012148, issued May 26, 2009.
Written Opinion for PCT/US2008/012148, mailed May 26, 2009.
Gdpawel, "Rare Cancer Support Forum", Jan. 1, 2006, XP055061044, retrieved on Apr. 25, 2013.
Holloway et al., "Association between in Vitro Platinum Resistance in the EDR Assay and Clinical Outcomes for Ovarian Cancer Patients", Gynecol. Oncol., 87(1):8-16 (2002).
Krishnamurthy S., "Applications of molecular techniques to fine-needle aspiration biopsy", Cancer (Cancer Cytopathology), 111(2):106-122 (2007).
Schayowitz et al., "Functional profiling of live melanoma samples using a novel automated platform", PLoS One, 7(12): e52760 (2012).
Weisenthal et al., "Platinum resistance determined by cell culture drug resistance testing (CCDRT) predicts for patient survival in ovarian cancer", pp. 1-25 (2003). Retrieved from the Internet: URL: http://weisenthal.org/w_ovarian_cp.pdf.
Weisenthal L., "Functional Profiling for Targeted Drug Therapy with Cell Culture Assays" (Nov. 20, 2006). Retrieved from the Internet: URL: http://www.weisenthal.org/Tokyo_Cancer_Symposium_Nov_2006_Weisenthal.pdf.
European Patent Office communication from EP 08 841 971.8, dated Sep. 9, 2013.

* cited by examiner

*Primary Examiner* — Galina Yakovleva
(74) *Attorney, Agent, or Firm* — DLA Piper LLP (US)

(57) ABSTRACT

Embodiments of the present invention are directed to improved methods and devices for analyzing a cell, aggregated cells, or a solid tumor. Such methods and devices are, for example, useful in the field of pathology and can provide improved cell processing and analytical results.

20 Claims, 22 Drawing Sheets

CARTRIDGE DESIGN ELEMENTS

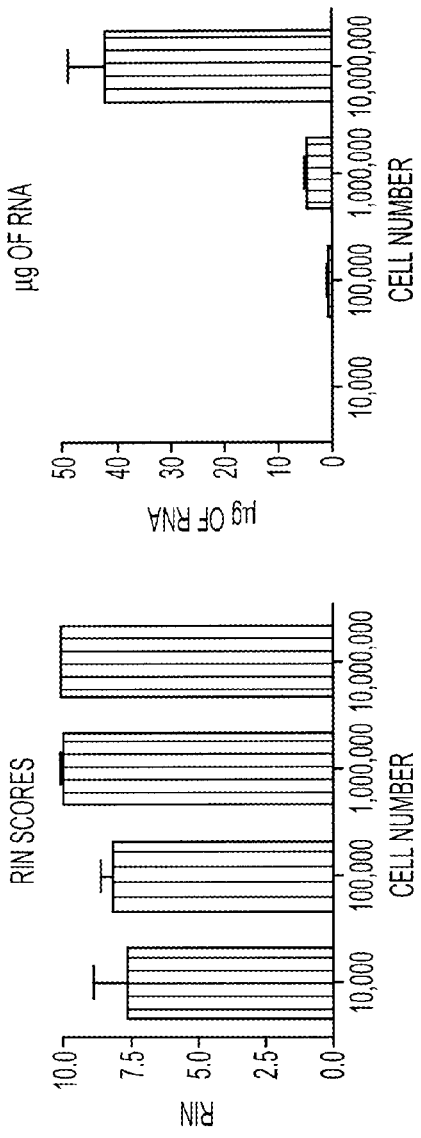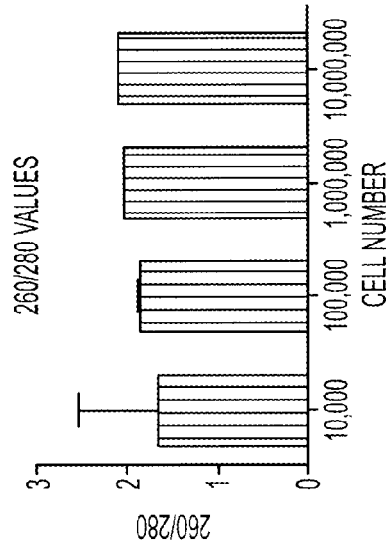
FIG. 13A
FIG. 13B
FIG. 13C

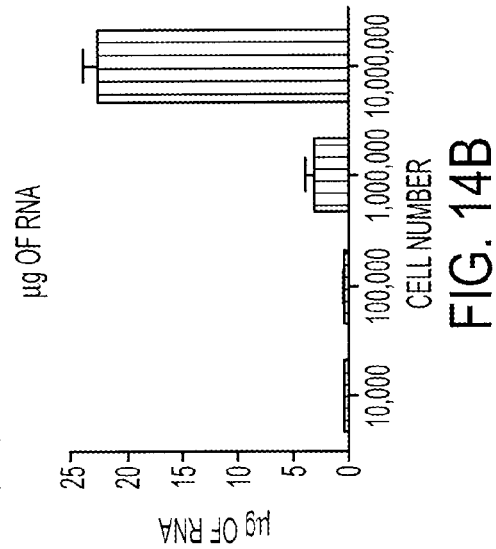
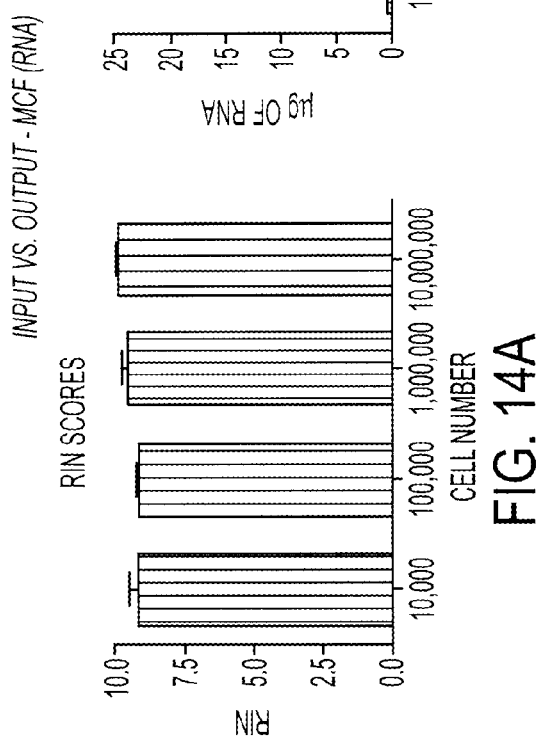
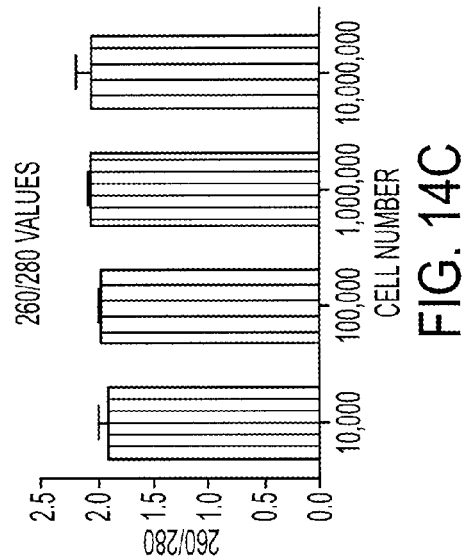
FIG. 14A
FIG. 14B
FIG. 14C

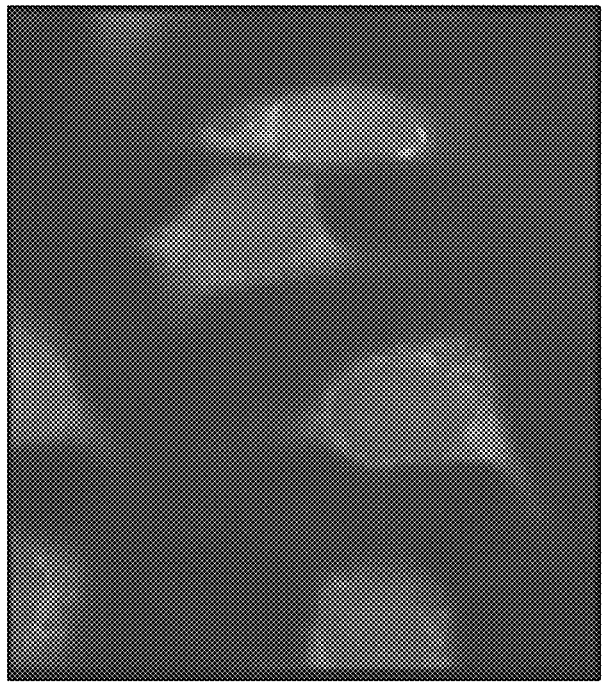

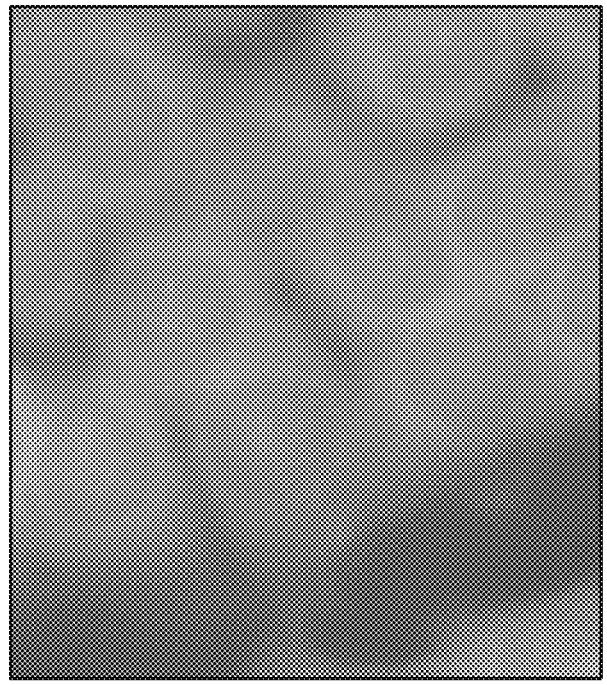
HCT-116 CELLS
FIG. 21A SnapPath PROCESSING
FIG. 21B 3 HOUR FORMALIN FIXATION

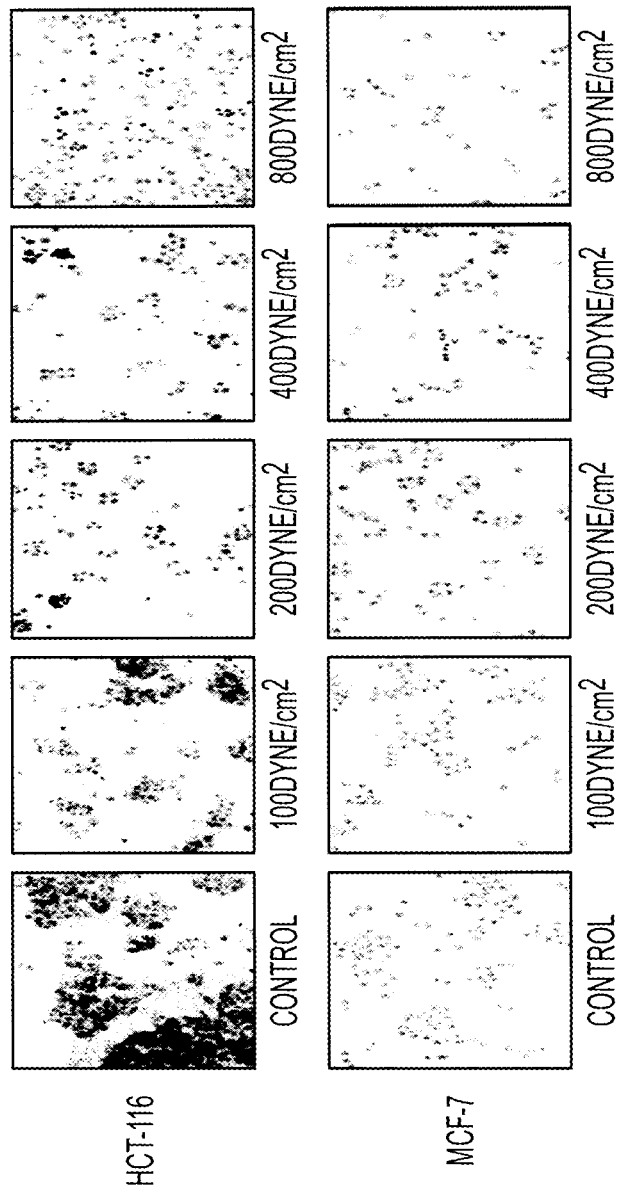

METHODS AND DEVICES FOR CELLULAR ANALYSIS

CROSS REFERENCE TO RELATED APPLICATIONS

This application claims priority to U.S. provisional application 61/099,059 filed Sep. 22, 2008 and U.S. provisional application 60/982,279 filed Oct. 24, 2007, the subject matter of both is incorporated herein by reference in its entirety.

FIELD OF THE INVENTION

Embodiments of the present invention are directed to improved methods and devices for analyzing a cell, aggregated cells, or a solid tumor. Such methods and devices are, for example, useful in the field of pathology and can provide improved cell processing and analytical results.

BACKGROUND

Traditional pathological samples have been largely processed using methods that involve killing the cells or lengthy sample processing times. Such methods are generally performed in a laboratory well away from the point of care. These traditional methods do not permit the examination of live cells, including dynamic, live-cell related biomarkers, and do not allow for rapid sample processing or analytical result generation at the point of care. This lack of complete and rapidly obtained information can prevent doctors from identifying the proper treatment regimen or at the least slow the process which adversely effects the patient's quality of life. A comparison of the traditional process to some improved embodiments is shown in FIG. 9.

For example, oncologists have a number of treatment options available to them, including different combinations of drugs that are characterized as standard of care, and a number of drugs that do not carry a label claim for a particular cancer, but for which there is evidence of efficacy in that cancer. The best likelihood of good treatment outcome requires that patients be assigned to optimal available cancer treatment, and that this assignment be made as quickly as possible following diagnosis.

While some cancers can be readily identified using genomic markers, reliable genomic markers are not available for all cancers, which may be better characterized as exhibiting abnormal expression of one or (typically) many normal genes. Currently available diagnostic tests to diagnose particular types of cancer and evaluate the likely effectiveness of different treatment strategies based on gene expression may have one or more disadvantages, for example: (1) the tests may be designed for testing blood and are not readily adapted for testing solid tumors; (2) sample preparation methods for solid tumor samples, including disaggregation of cells, may be unsuitable for handling live cells or performing subsequent measurements of marker expression; (3) small samples, e.g., obtained using fine needle biopsies, may not provide sufficient tissue for complete analysis; (4) the tests may require in vitro culturing of the cells, extended incubation periods, and/or significant delays between the time that the test cells are obtained from the patient and the time the cells are tested, resulting potential for wide variation and external influences on marker expression; (5) the tests may be unsuited for measuring expression of a multiplicity of genes, phosphoproteins or other markers in parallel, which may be critical for recognizing and characterizing the expression as abnormal; (6) the tests may be non-quantitative, relying principally on immunohistochemistry to determine the presence or absence of a protein as opposed to relative levels of expression of genes; (7) the reagents and cell handling conditions are not strictly controlled, leading to a high degree of variability from test to test and lab to lab; (8) the tests may be unsuited to analyzing RNA levels, due to the instability of RNA and the practical difficulty of obtaining sufficiently fresh samples from the patients; and (9) the tests may involve fixing of the cells before any gene expression analysis can be performed, e.g., in the presence or absence of selected reagents.

Recently, several groups have published studies concerning the classification of various cancer types by microarray gene expression analysis (see, e.g. Golub et al., Science 286: 531-537 (1999); Bhattacharjae et al., Proc. Nat. Acad. Sci. USA 98:13790-13795 (2001); Chen-Hsiang et al., Bioinformatics 17 (Suppl. 1): S316-S322 (2001); Ramaswamy et al., Proc. Natl. Acad. Sci. USA 98:1514915154 (2001)). Certain classifications of human breast cancers based on gene expression patterns have also been reported (Martin et al., Cancer Res. 60:2232-2238 (2000); West et al., Proc. Natl. Acad. Sci. USA 98:11462-11467 (2001); Sorlie et al., Proc. Natl. Acad. Sci. USA 98:1086910874 (2001); Yan et al., Cancer Res. 61:8375-8380 (2001)). However, these studies mostly focus on improving and refining the already established classification of various types of cancer, including breast cancer, and generally do not provide new insights into the relationships of the differentially expressed genes. These studies do not link the findings to treatment strategies in order to improve the clinical outcome of cancer therapy, and they do not address the problem of improving and standardizing existing techniques of cell handling and analysis.

Although modern molecular biology and biochemistry have revealed more than 100 genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients to treatment with anti-estrogen drugs, such as tamoxifen. Another exceptional example is the use of ErbB2 (Her2) protein expression in breast carcinomas to select patients with the Her2 antagonist drug Herceptin® (Genentech, Inc., South San Francisco, Calif.). For most cancers, however, the pathologies in gene expression may be subtler and may involve patterns of expression of multiple genes or expression of genes in response to particular stimuli.

The challenge of cancer treatment remains to target specific treatment regimens to pathogenically distinct tumor types, and to identify the optimal treatment as early as possible in order to optimize outcome. Hence, a need exists for tests that simultaneously provide prognostic and/or predictive information about patient responses to the variety of treatment options.

There is a need for a device and a method to prepare solid tumor biopsies or otherwise aggregated cells which address these disadvantages and integrate, in a single small and compact apparatus, the function of handling and preparing tissue samples using controlled, consistent and efficient steps; maintaining viability of the tissue sample, to permit stimulation and/or preservation of different biomarker responses from the same tissue sample before the sample loses viability or becomes cultured through ex vivo replication.

SUMMARY

Embodiments of the present invention are directed to methods for processing or preparing a live tissue sample of aggregated cells from a subject. These methods can include: disaggregating and dispersing an aqueous solution containing live aggregated cells obtained from a subject into at least one test aliquot in a first isolated chamber; optionally purifying the aliquot to increase the percentage of target cells relative to other contaminating cell types by removing the contaminating cells; distributing the optionally purified live cells into one or more second isolated chambers for analysis; and stabilizing the distributed cells to permit cellular and/or molecular analysis of the distributed cells.

The present invention is also directed to, in some embodiments, methods for processing or preparing cancer cells from a solid tumor that include: disaggregating and dispersing live cancer cells obtained from a solid tumor into at least one test aliquot in at least one first isolated chamber; optionally purifying the live cancer cells to remove contaminants; distributing the live cancer cells into one or more second isolated chambers for analysis; and stabilizing the distributed cells to permit cellular and/or molecular analysis of the cells.

Further, some embodiments of the present invention are directed to cartridges for cellular processing. For example, cartridges for use in processing or preparing live cancer cells having a plurality of sterile compartments, wherein the compartments can be separated from one another. Other embodiments are also directed to cartridges having a plurality of compartments including: a compartment for dispersing cells, a compartment for purifying cells, and a compartment that is an isolated chamber.

The invention is also directed to systems including a cartridge of the present invention and an analytical device. Kits including the cartridges of the present invention are also encompassed herein.

BRIEF DESCRIPTION OF THE DRAWINGS

FIG. 13 shows RIN scores 13A, μg of RNA produced 13B, and 260/280 values 13C in HCT-116 cells at varying cell numbers.

FIG. 14 shows RIN scores 14A, μg of RNA produced 14B, and 260/280 values 14C in MCF-7 cells at varying cell numbers.

FIG. 20 shows the results of using live cell probes in MCF-7 cells prepared using the present methods versus those prepared using a three hour formalin fixation procedure.

FIG. 21 shows the results of using live cell probes in HCT-116 cells prepared using the present methods versus those prepared using a three hour formalin fixation procedure.

FIG. 22 shows an example dispersion of MCF-7 and HCT-116 cells using the disaggregation techniques described herein.

DETAILED DESCRIPTION

Embodiments of the invention described herein include, but are not limited to, an automated, self-contained, fluidic tumor cell processing and testing system that promotes the development and use of targeted therapies and molecular diagnostic tests. Embodiments of this invention also include methods of using the system, including improved pathological processing methods that can be performed on live cells ex vivo. The present invention is also directed to kits for use with the system and methods described herein.

The invention provides a safe, effective, accurate, precise, reproducible, inexpensive, cost effective, efficient, fast and convenient method and "cartridge-based" system for collecting, handling and processing of solid cellular specimens ex vivo. These methods and cartridges can maintain viability of the samples during the process to maintain biomarker integrity, and optionally, evoking biomarkers such as phosphoproteins and RNAs not present in original sample thru ex vivo stimulation. The invention provides fully integrated specimen and information management in a complete diagnostic cytology laboratory system and controlled conditions following biopsy, which minimizes variability between tests, minimizes the risk of biocontamination, and minimizes the effect of the sample preparation process itself on biomarker expression. Embodiments of the present invention can be used to facilitate targeted treatment of the tumors, and optionally also provide a tissue sample adequacy evaluation such as a cell-count function and/or other connected analyses.

Figure 9:
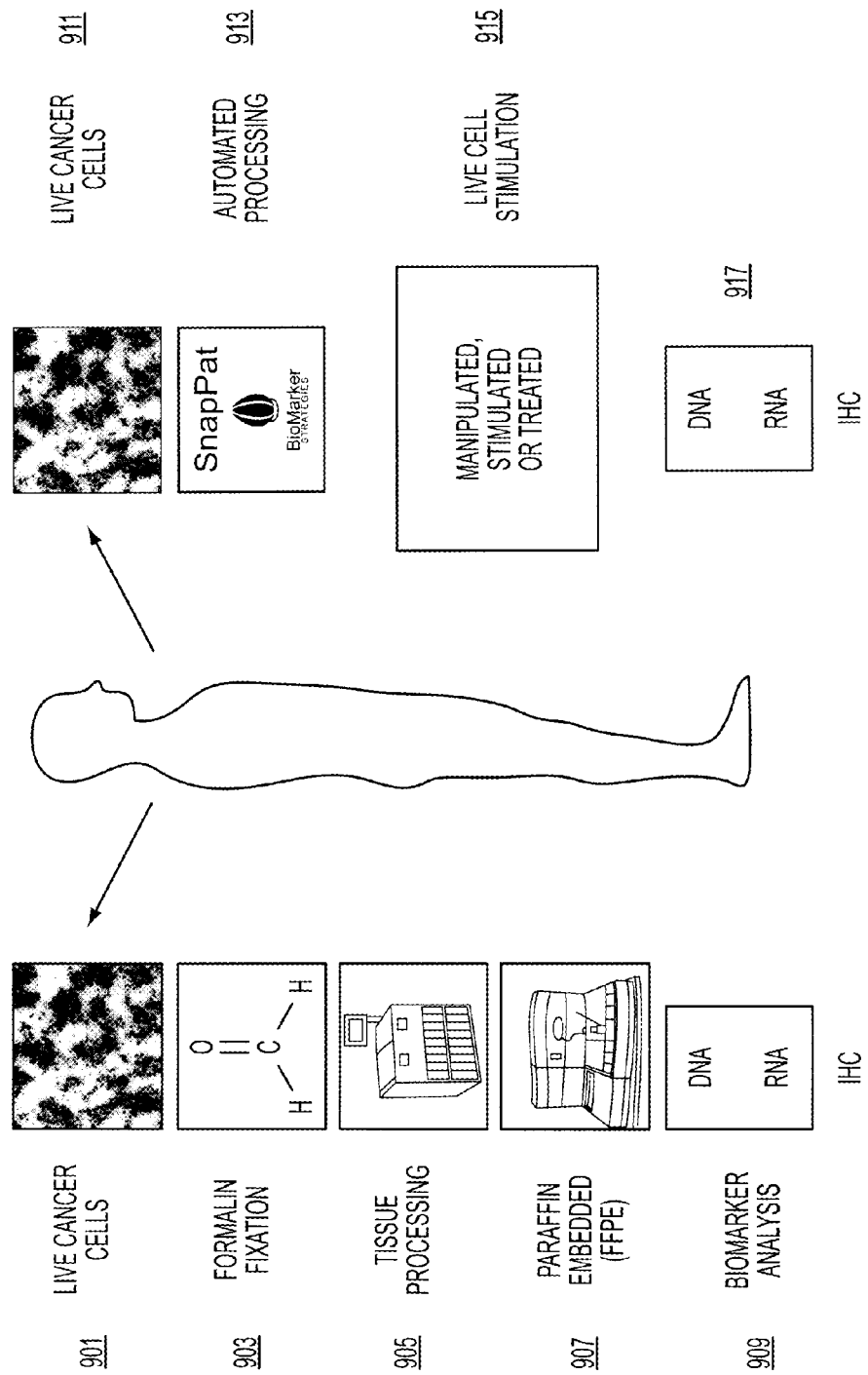
FIG. 9 shows a comparison of a traditional pathology sample processing method (left) with an example processing method of the present invention (right).
Figure 10:
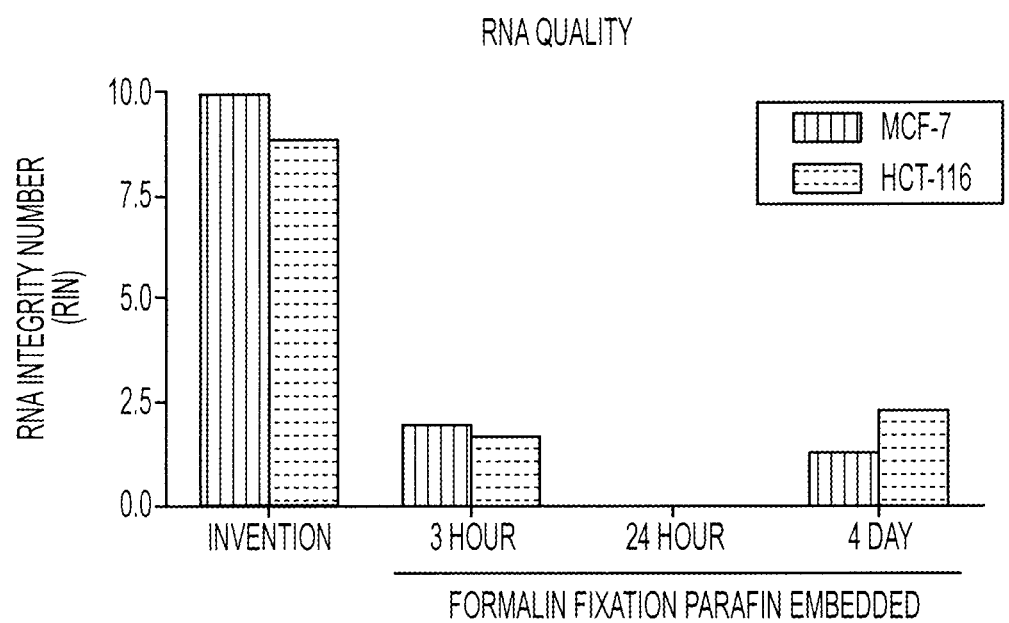
FIG. 10 shows that the methods of the present invention produce RNA samples having a higher RNA integrity number (RIN) than a formalin fixation paraffin embedded process.
Figure 11:
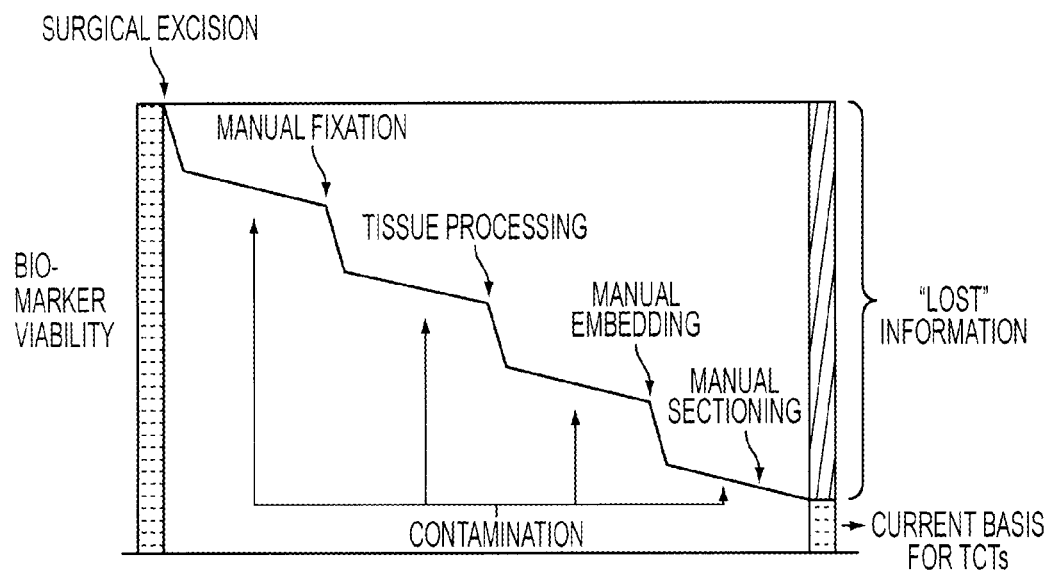
FIG. 11 provides an illustration showing that traditional tumor sample processing methods can damage biomarkers which can reduce the cellular information available.

As illustrated in FIG. 9, traditional cell processing techniques can use formalin fixation prior to tissue processing and eventually embed the cells in paraffin. This results in a lot of potential cellular information being "lost" as shown in FIG. 11. However, the improved methods described herein and depicted for example in FIGS. 9 and 12 allow for automated processing of live cells, stimulation of these cells, and then analysis of the cells using the methods described below.

As one of skill in the art will appreciate, these novel devices, systems, kits and methods can provide numerous advantages in a clinical or research setting. For example, they can be used to provide immediate, near patient, biopsy processing without the need to send the specimen to a remote laboratory. They can also be used to standardize and automate biopsy processing in a cost effective manner. The present invention can provide more detailed molecular information about the cells than current pathological processes allow which enables greater sub-classifications of cells in a biopsy (e.g., cancer cells), optionally using new ex vivo biomarkers and diagnostic tests. Taken together, the advantages of the present invention allow for a rapid diagnosis at the point of care and the subsequent creation of more effective patient specific treatment regimens.

Figure 12:
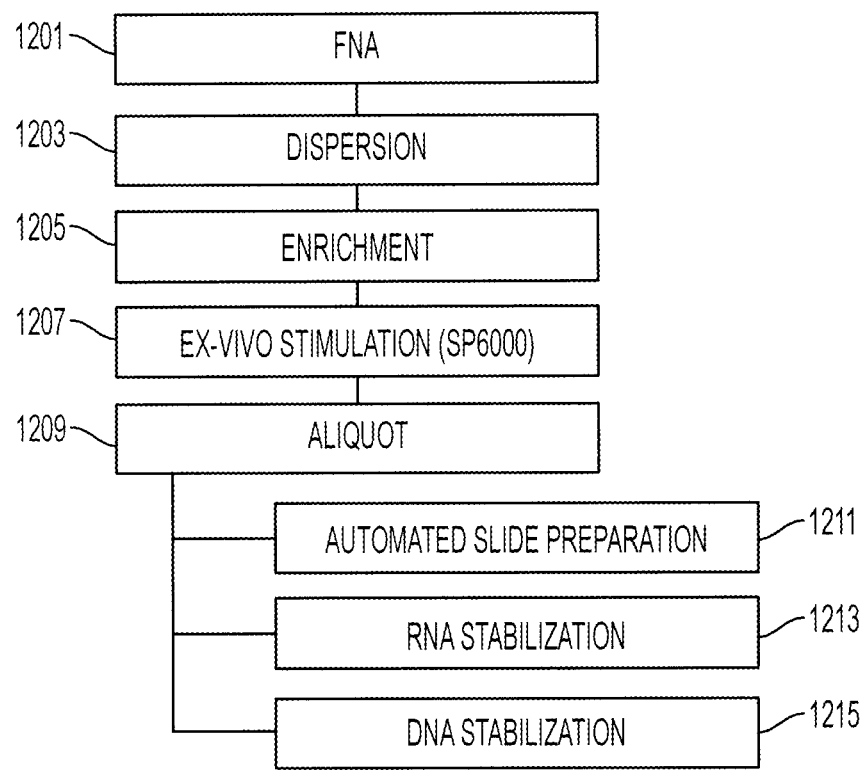
FIG. 12 shows an example processing method of the present invention that begins with extraction using fine needle aspiration (FNA).

An example, non-limiting process for using for the devices, systems, and methods, which are described in more detail to follow, is shown in the flow chart in FIG. 12. The process can begin by obtaining a sample of aggregated cells such as the Fine Needle Aspiration (FNA) step 1201 shown in FIG. 12. The sample is then disaggregated using the novel techniques described herein and then dispersed 1203 into isolated chambers. If the sample contains a mixture of cells of interest and other cells, the sample can be optionally purified to enrich 1205 the number of cells of interest in the sample by removing contaminants and cells that are not of interest. The sample can then be optionally stimulated ex vivo 1207 or otherwise mixed with a test reagent and then aliquots are placed into new isolated chambers 1209. The aliquots can also be optionally stimulated ex vivo or otherwise mixed with a test reagent depending on the assay being performed. The aliquots are then analyzed for a property of interest. For example, slides can be prepared from the aliquots for microscopic analysis 1211 or aliquots can have their cells lysed and the nucleic acids, RNA and DNA, analyzed, 1213 and 1215, respectively. The results of the analysis are then communicated to the researcher or clinician who can take appropriate action, for example, setting a treatment regimen for a patient from which the FNA was taken. Further, as illustrated in FIG. 11, the improved methods and devices disclosed herein can allow a researcher or clinician access to new information that is "lost" during traditional pathological cell processing techniques.

I. Devices, Systems, and Kits

A. Devices

In a further embodiment, the invention provides a device or platform, which is useful, e.g. in the methods of processing and/or preparing live cells described herein. This device is also referred to as a cartridge. Some embodiments of the devices of the present invention are described in more detail below and depicted in FIGS. 1-8.

Such cartridges can contain one or more isolated chambers. An isolated chamber is any compartment, section, or other utility holder than can hold a sample of live cells or a sample of fixed, processed, and/or stabilized cells. For example, the term isolated chamber includes, but is not limited to, wells, vials, tubes, slides (e.g., glass), and plates.

The isolated chambers or compartments of the present invention are suitable for one, some or all of the following functions: (1) receiving biological specimens via a septum or other sealed chamber; (2) contained and secured syringe needle storage; (3) liquid reagent storage available for removal via septum; (4) waste receipt and storage via septum; (5) sample disruption via liquid shear and mechanical shear; (6) cell counting and cell visualization; (7) bead based separations, and (8) containing solid resins.

Each cartridge can contain one or more isolated chambers depending on its use. For example, a cartridge can have between 1 and about 200 isolated chambers, between about 1 and 100 isolated chambers, or between about 1 and 50 isolated chambers. Some embodiments have about 24, about 48, or about 96 isolated chambers.

Figure 2:
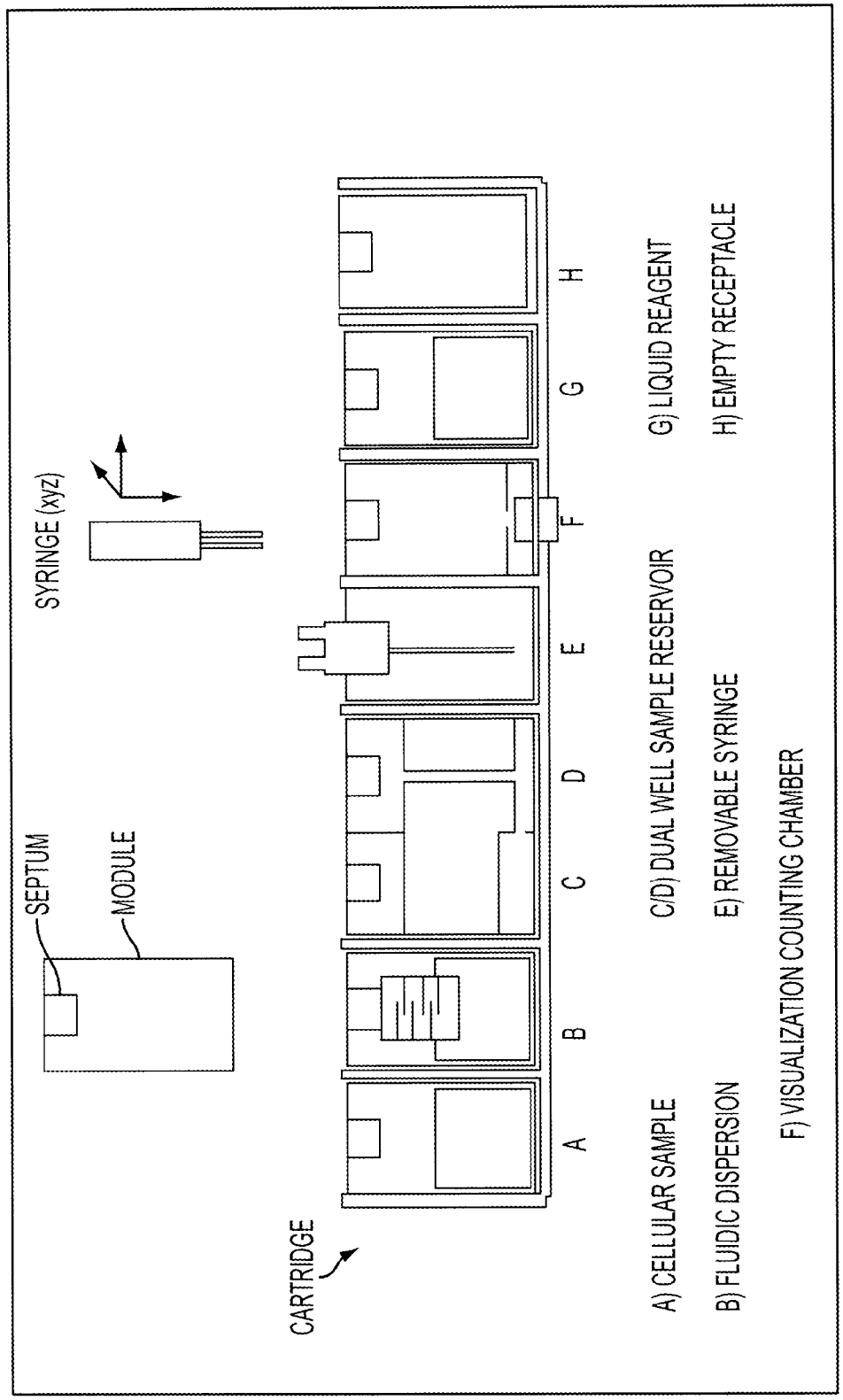
FIG. 2 shows exemplary isolated chambers within a cartridge for receiving and handling a sample.
Figure 3:
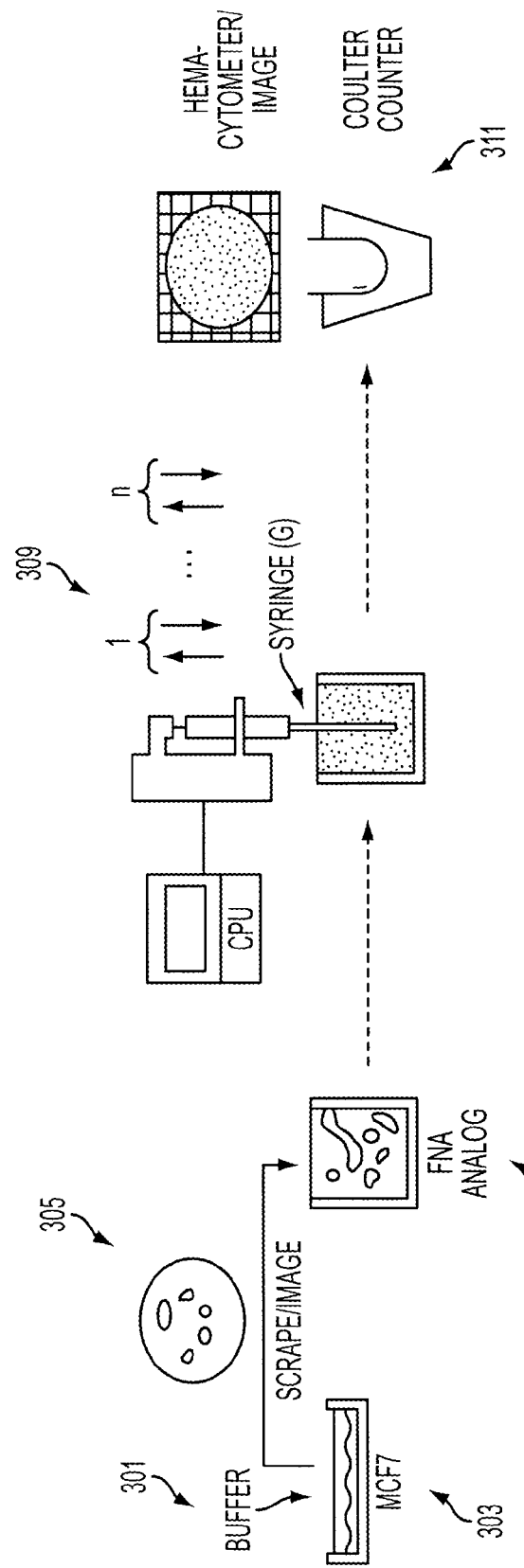
FIG. 3 shows an example disaggregation process according to the invention.

In some embodiments, a cartridge has one or more of a first isolated chamber and one or more of a second isolated chamber. A cartridge can have a first isolated chamber for holding a sample of cells. Such a cartridge can also feature one or more second isolated chambers which hold the dispersed aliquots of the cell sample. In some embodiments, the second isolated chamber can contain a predetermined amount of a test reagent in the chamber before the dispersed aliquot of cells is added. FIG. 2 illustrates exemplary isolated chambers that may be present for receiving and handling a sample.

Figure 7:
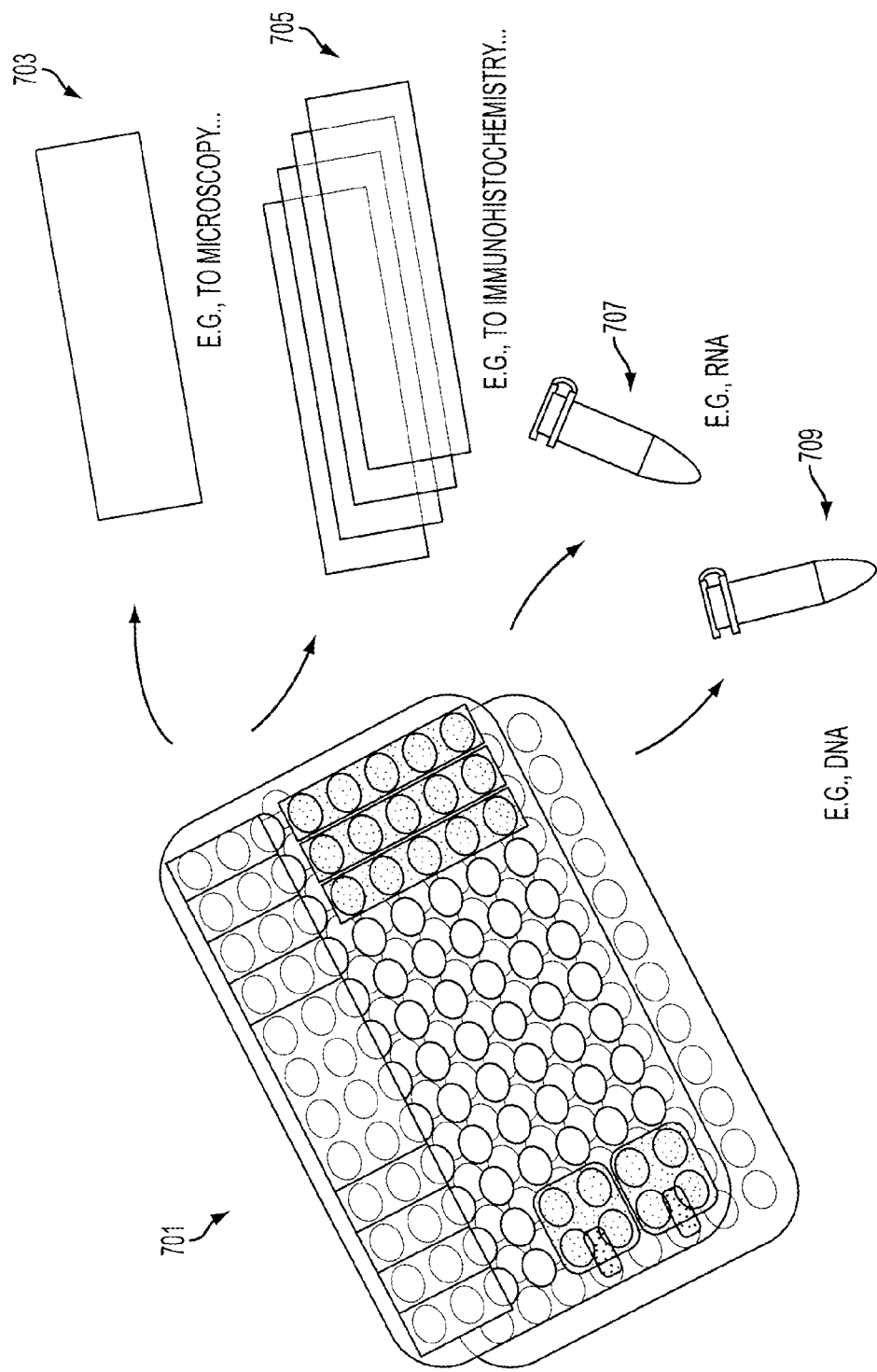
FIG. 7 shows an example view of an embodiment of the cartridge of the present invention where some of the compartments of the cartridge can be separated from one another.

In one embodiment the invention provides a cartridge having compartments (e.g, isolated chambers) that can be separated from one another. As illustrated in FIG. 7, the compartments can be separated and the sample inside may be used for different analytical tests. For example, one compartment can be sent for DNA analysis, another for RNA analysis, another for microscopic analysis, and another for immunohistochemical analysis. For example, the second isolated chambers on a cartridge can be separated from the first isolated chamber in some embodiments.

The devices of the present invention can contain a heating element to maintain the temperature of the cartridge at a desired temperature, for example, between about 30° C. and 40° C., between about 36° C. and about 38° C.; or any other desired temperature.

Figure 4:
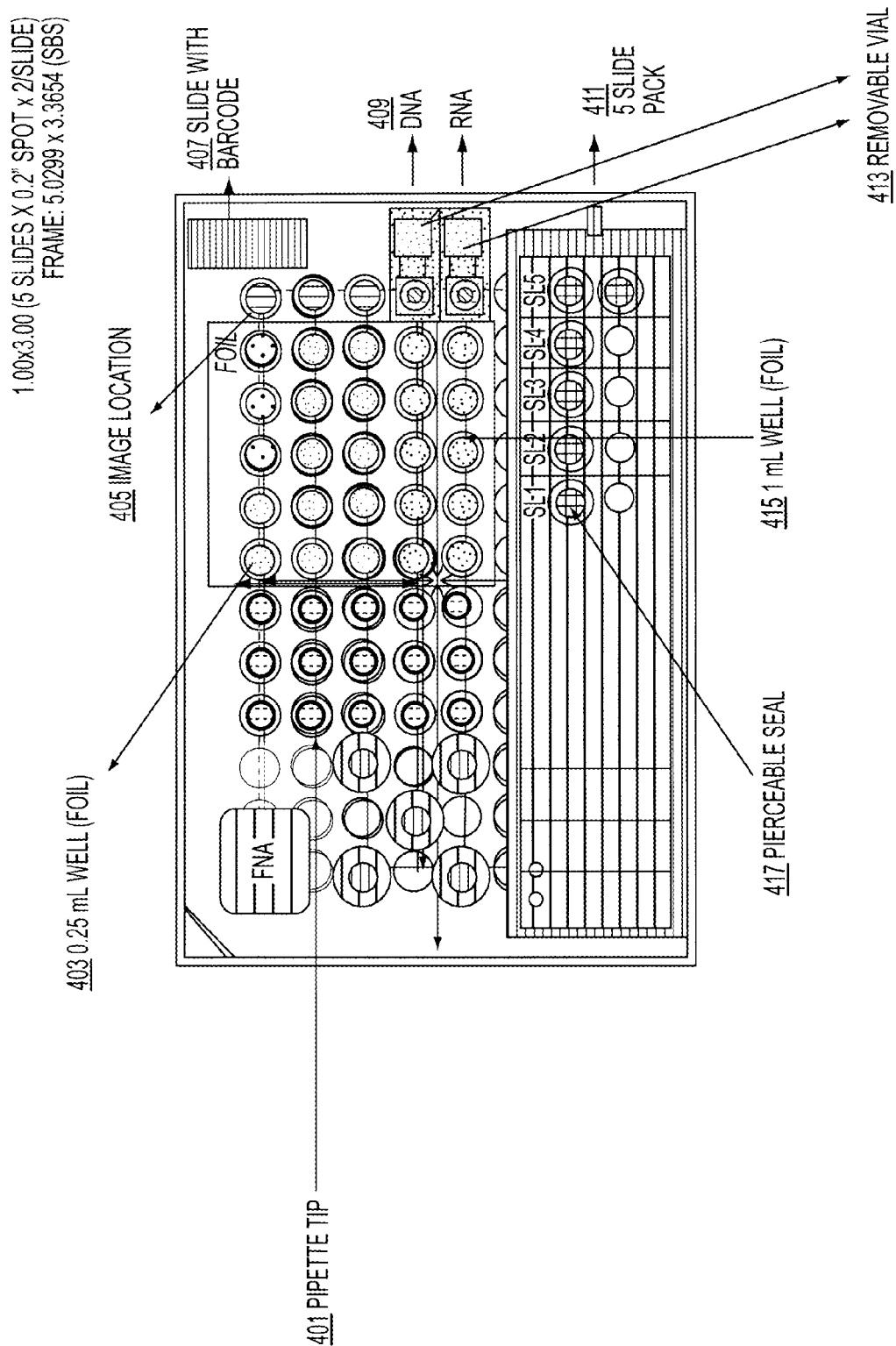
FIG. 4 shows an additional embodiment of a cartridge of the present invention.

The devices of the present invention can contain a barcode or other means of indentifying the cartridge and/or the source of the sample of cells in the device. The barcode or others means of identifying the cartridge can be used to facilitate specimen identification and/or patient safety. Such means of identification can interact with computer based data storage systems, automated cell processing systems and/or assays, and personal digital assistants. An example embodiment of a cartridge having a barcode is depicted in FIG. 4.

Some embodiments of the device can include a cell counting mechanism, as depicted, for example in FIG. 2F. These mechanisms can be automated systems or manual systems. For example, the cell counting mechanism can be a hemocytometer or a Cellometer® (available from Nexcelom Biosciences, LLC) and potential digital or optical based counting. As one of skill in the art will appreciate, other methods of counting cells are well known in the art and can also be used with the present invention.

The cartridges of any embodiment of the present invention can have one or more modules or isolated chambers that contain resins, reagents, solvents, and other materials. A module may be a single isolated chamber or a set of a plurality of isolated chambers used for a particular purpose. For example, where multiple manipulations (e.g. lysing and staining) are involved for a particular test, more than one isolated chamber may be used as part of that test "module." For example, one or more isolated chambers can contain resins with attached nucleic acids, proteins, natural or synthetic polymers or small molecules. One or more isolated chambers can contain liquids, e.g. buffers, molecular biology enzymes, biological molecules including nucleic acid or proteins, or small molecule chemicals. One or more isolated chambers can contain dry reagents for on-cartridge solubilizations, e.g. where dry reagents may include nucleic acid, proteins, natural or synthetic polymers or small molecules.

In some embodiments, a camera or other digital imaging device is part of the cartridge or can be used with a cartridge. Accordingly, the cartridges of any embodiment of the present invention can include an imaging module that allows cell visualization and digital image based cell counting (see FIG. 2F) on samples of volumes between 10 and 500 microliter and said volume is dispensed into imaging cell by positive displacement or by capillary action. The imaging device can also be used to take pictures of the sample, e.g., cellular components within the sample such as protein localization data.

The cartridges of any embodiment of the present invention can have a fluidic module that passages cells through micropassages with diameters of 10 to 500 microns to create wall shear stresses of 100 to 800 dynes/cm2 using volumes between 10 and 1000 microliters.

The cartridges of any embodiment of the present invention can have an immunodepletion module or isolated chamber. Such an immunodepletion module or isolated chamber can utilize magnetic beads or other methods. See, e.g., the magnetic bead products available from Dynal Biotech, Oslo, Norway. These embodiments are described in more detail in the methods section.

The cartridges of any embodiment of the present invention can have one or more modules or isolated chambers that contain or are designed to contain a biological specimen which can be, for example, a fine needle aspiration biopsy, core biopsy, biological fluid sample such as saliva, blood, semen, or vaginal fluid, harvested tissue from an organism, or cell culture sample. Such a module can also be referred to as the first isolated chamber and is depicted, for example, in FIG. 2A and in FIG. 4.

In a further embodiment, the invention provides cartridges, e.g. suitable for use in the methods and devices described herein, for example having individual and self-contained modules, the modules containing media suitable for cell handling and being each sealed by a septum or other sealing mechanism, said septum or sealing mechanism being capable of being bypassed or perforation by a tube, e.g., needle, and resealing upon removal of the tube. In some embodiments, there are sufficient modules or isolated chambers to permit unified delivery and removal of all liquid reagents, biological test specimens, sharps (i.e. needles), etc. into and out of the cartridge or an analytical device enclosing the cartridge where the analytical device provides biohazard containment during analysis. Modules can contain a number of isolated chambers with associated reagents and devices for performing specific tests or activities such as cell counting or viability assay. The embodiments described above are depicted, for example, in FIGS. 1,2, 4, 6, 7, and 8.

Figure 5:
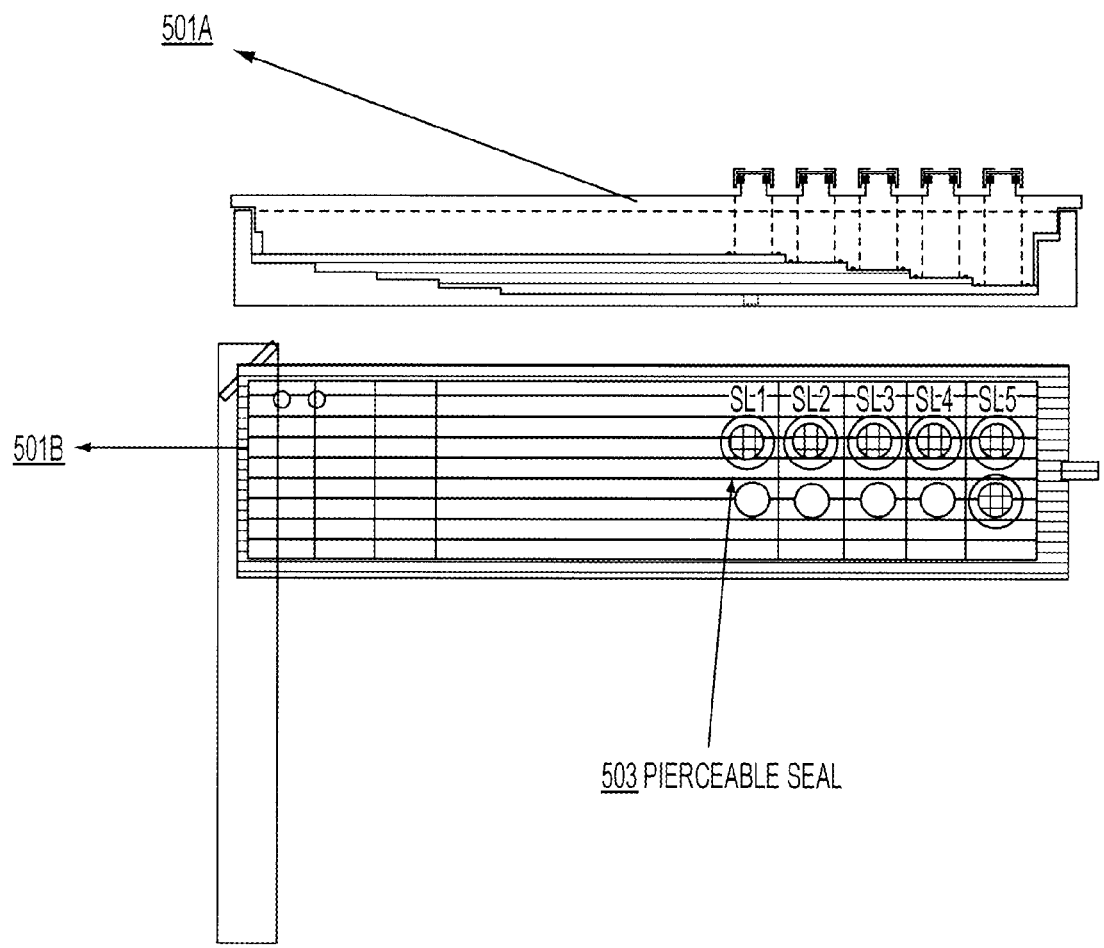
FIG. 5 shows a cross section and top view of an exemplary embodiment of a glass slide holder that can be positioned on a cartridge of the present invention.
Figure 6:
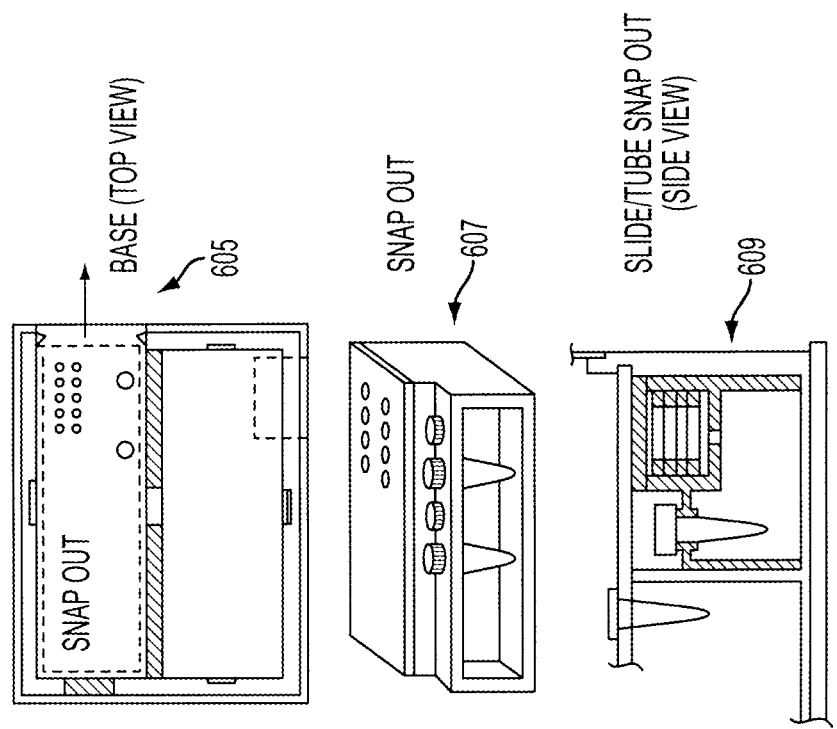
FIG. 6 shows an additional embodiment of a cartridge of the present invention illustrating exemplary features.
Figure 6:
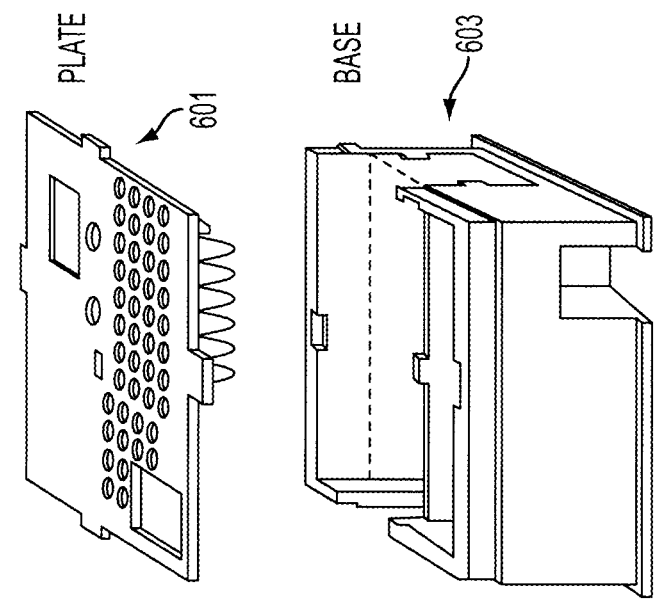

As shown in FIG. 5, 501B, the cartridges of the present invention can have slides stacked in, for example, a staircase configuration 501A that enables the slides to be efficiently utilized to accept cellular material then subsequently accessed and removed singly by manual or robotic means. FIG. 5 shows a cross section illustrating the staircase configuration 501A/B. Thus in a further embodiment, the invention provides a device which comprises a holder containing a multiplicity of planar substrates, e.g., glass slides, arranged in a staircase configuration, wherein the holder restricts lateral and vertical movement of substrates. Suitable substrates include, but are not limited to, flat rectangular pieces such as glass slides, metal plates, or microfluidic devices. The substrates can have a thickness between 0.1 and 3 mm and/or dimensions of 2-3 cm wide by 7-9 cm long. As one of skill in the art will recognize, other substrates or isolated chambers may be arranged in a similar manner on the cartridges and such embodiments are encompassed herein.

In some embodiments, the holder on the cartridge has a bottom portion and a lid portion with each portion containing stair steps for positioning and preventing movement of a staircase stack of individual substrates within the holder or relative to the holder. When stored in the holder, the substrates can have a distal end where the bottom-most portion protrudes beyond the stack (see FIG. 5 at 501B). This distal end can have one or more printed features, wells or depressions. These printed features can be labels for identifying the substrates once they have been used or prior to use. In some embodiments, the holder has a lid and the distal end of the substrate is exposed to access through a septum or septa of the lid. The holder can be mounted and dismounted into a frame, for example, a frame with an SBS-compatible footprint. Optionally, the holder can have a small hole or plurality of holes in the bottom.

FIG. 5 illustrates a top view of an exemplary holder. The stack of slides can be addressable from above according to standardized row and column spacing making the system ideal for automated or manual use. The holder can have a lid with septa above each substrate for addressing positions above each substrate independently. For example, the holder can have an O-ring or gasket sealable chamber above each addressable position of each substrate. These O-ring or gasket sealable chambers can be of any shape desired, for example, circular or rectangular or square.

Positioning the holder and substrates in a predetermined manner can allow multiple delivery of fluid sample of volumes ranging from 1 nanoliter to up to 0.5 milliliter to the substrate through the use of a pipette, syringe needle, or pintool. The holder, in some embodiments, restricts lateral or vertical displacement of substrate during fluid delivery and restricts movement of substrate during fluid delivery. In other embodiments, the holder permits vertical rotation but restricts lateral movement of substrates. This flexibility can allow automated or manual multiple fluid delivery to and removal from each isolated chamber using a wide array of methods and systems.

In some embodiments, the holder can be disassembled with the lid portion removed and the bottom portion can be mounted on a stand that positions a protrusion through the hole in the bottom portion of the holder. The substrates can be uniquely presented while on the stand protrusion for sequential gripping by human hand or a robotic grip tool. This allows for sequential removal of substrates, e.g., bottom slide first and top slide last, to prevent scraping of substrates over deposited samples on each sample thereby allowing stable transportation of slide-based cellular material. Example disassembled views of cartridges having embodiments of the above described holder are disclosed in FIGS. 6 and 8.

The fluidic samples can be delivered to the substrates in an automated system or manually. In some embodiments, the fluidic samples are sequentially delivered to the substrates in a predetermined order. Suitable fluidic samples include, but are not limited to, solutions, emulsions, suspensions, or polymer-containing mixtures. For example, the fluidic sample can be, but is not limited to, biological or chemical materials, e.g., small organic or inorganic molecules, proteins, nucleic acid, cells, particles, volatile and non-volatile solvents, polymers, or fixatives.

In a further embodiment, the invention further provides well plates useful in the cartridges of the invention. Currently, there is a need for a well plate technology that allows components (open tubes, sealed tubes, syringes, pipette tips, etc) to be locked in position so that they will not fall out of position if the plate is held sideways or upside down. Furthermore, well plate technology allows the locked-in component to be removed by a standard (Cartesian) pipette tool, utilized, and then returned to a locked-in position, without requiring even a tip ejector on the pipette tool. In some embodiments, the present invention is directed to a well plate comprising a planar surface with a multiplicity of wells that is manufactured such that two adjacent positions (called "dual well") on the well plate are connected by an intervening space allowing lateral transit of a component.

The component can be an open tube, sealed tube, tube with septums, transparent tubes, any container, syringe, needle, blade, or pipette tip. In some embodiments, the component contains a rigid piece of material of square, circular, or other shape of suitable thickness to pass through a locking mechanism and conforms to the shape of the locking mechanism of a lock-in well.

In some embodiments of the dual-well plate, the first adjacent position of the dual well (called a "lock-in well") contains small tabs that allow components to be locked in position and resist movement, especially withdrawal of the component in the vertical direction when the plate is facing upward. These dual-well plates can also have a lock-in well containing a compliant gasket that is partly compressed when a component is locked into the lock-in well and this gasket prevents movement of the locked-in component.

In some embodiments, the component contains a "fitting" addressable by a tool (e.g., a pipettor or syringe) wherein the fitting (e.g., a luer lock) allows a snug and airtight fit with the tool. The tool can mount the component that is locked into the lock-in well and push down on the component to further compress the gasket thereby allowing the component to reside in a position that allows lateral transit within the intervening space of the dual well from the first position (lock-in well) to the second position of the dual well, called the "release well." In some embodiments, the component can freely travel out of and into the release well when moved vertically by the tool. The tool can also deliver a component fully into the lock-in well and, when the well plate is anchored to a surface, the tool can move vertically away from the wellplate, thereby dismounting the component while the component is locked in the lock-in well.

The tool and the plate can each be mounted on a computer controlled gantry system allowing movement of the tool and/or plate in Cartesian coordinates (x, y, z) thereby allowing the tool to deliver components to the lock-in well and then leave components in the lock-in well, mount components in the lock-in well and move them to the release well, remove components from release well and free them from the well plate. Such a setup can also allow the tool to deliver components to the release well and leave components in the release well by means of a tip ejector.

Some computer-controlled systems using the tool and plate can be set up to not require the use of angular motion (theta-axis) thereby preventing positional rotation reorientation of the component with respect to the well plate while the component is in the well plate or removed from the well plate.

In some embodiments, the dual-wells can be used to allow fluid to flow through a predetermined path that has been designed to remove contaminants from the sample. Such a dual well system is illustrated, for example, in FIG. 2 at wells C and D.

B. Systems

The present invention is also directed to systems that utilize the cartridges and methods described herein. For example, a system can include one or more of the inventive cartridges, either individually or as part of a kit, and an analytical device (also referred to herein as an apparatus) capable of interacting with the cartridge to obtain at least one analytical result. For example, the system can be used at the point of care to obtain a medical diagnosis for a patient.

Figure 1:
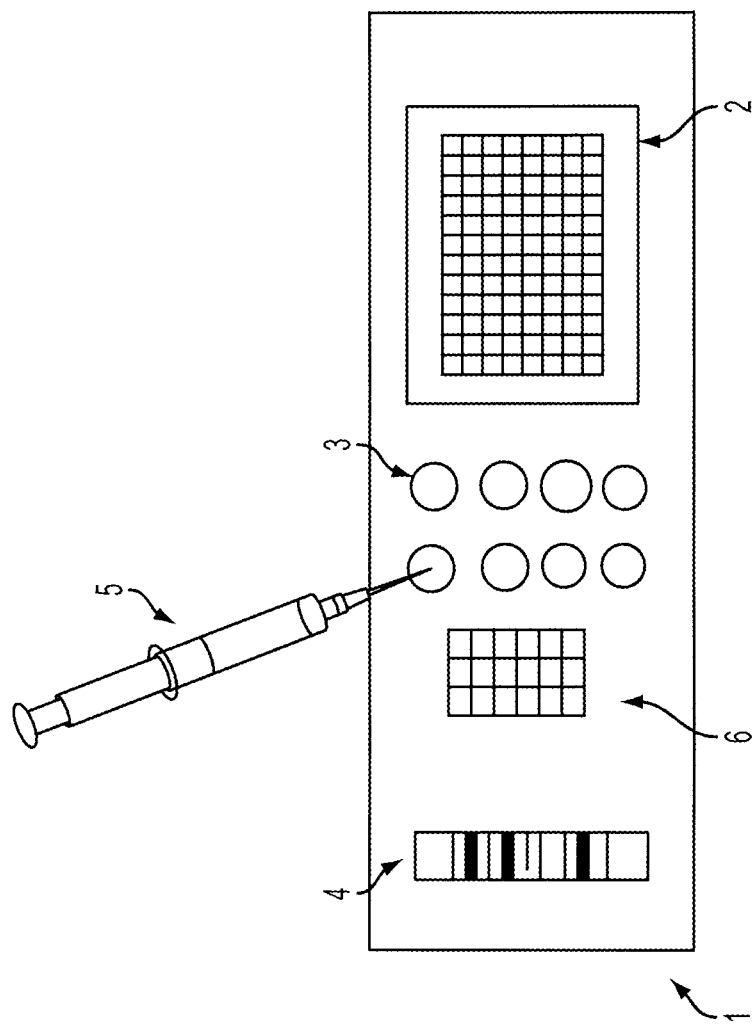
FIG. 1 shows an example embodiment of a cartridge of the present invention.
Figure 8:
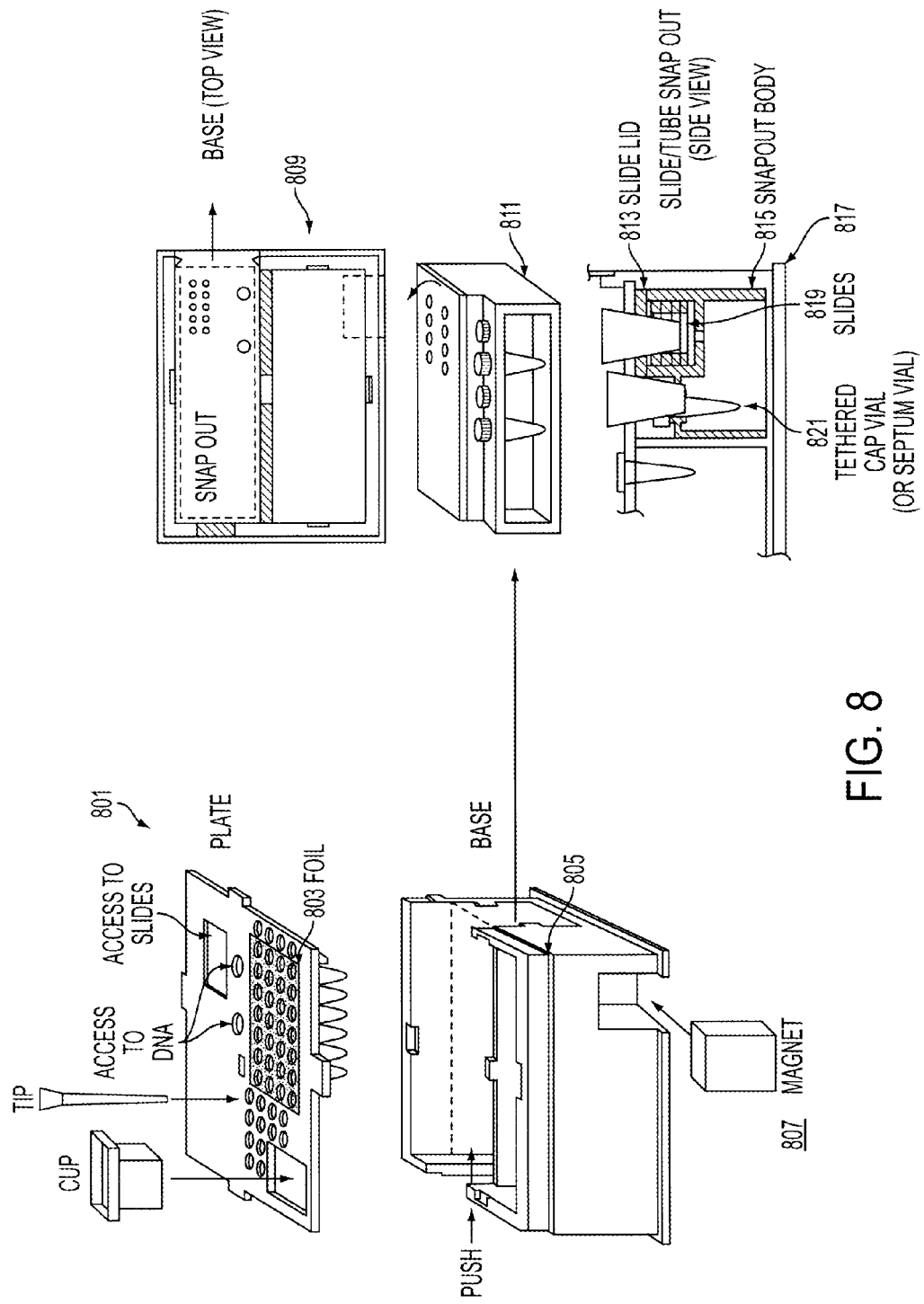
FIG. 8 shows an additional embodiment of a cartridge of the present invention illustrating exemplary features.

Accordingly, some embodiments of the invention are directed to an analytical device for performing operations on a cartridge containing individual modules (e.g. isolated compartments) wherein the device comprises one or more holders for one or more syringes, the syringes having hollow needles and being oriented above a platform on which the cartridge is located such that the needles can be directed to individual modules of the cartridge using a Cartesian coordinate system (x, y, z) by computer controlled motion control to apply suction and dispense contents to the modules of the cartridge, the modules each having a septum which can be penetrated by the needles, but which otherwise isolates the contents of the modules from the environment. Examples of some embodiments of these cartridges are depicted in FIGS. 1, 4, and 8. In some embodiments the holder can pick up a syringe or tool provided by the cartridge.

The analytical device can have a means for receiving a cartridge of the present invention. For example, a slot, opening, hole, or other area capable of receiving a cartridge. Once a cartridge has been placed in the means for receiving, in some embodiments, a door closes to seal the means for receiving and thereby fully enclosing the cartridge within the analytical device. This door closure can be manually performed or automatic. These fully enclosed versions can be especially useful in preventing potential biohazards from being spilled or otherwise released into a lab or clinical environment.

In some embodiments, the systems for using the analytical device and cartridge do not require or use vacuum utility; air service utility; natural gas utility; and can be free of all reagents lines (process fluid, analytical reagents, and waste streams) and attached bottles. That is, the device is fully self contained.

The cartridges used in such a system, or used independently, can also be self-contained. This means the cartridge comes pre-loaded with all necessary tools (e.g., pipette tips) and reagents (e.g., a test reagent, dye, or other compound) required to perform a desired assay either manually or using an automated system. For example, the cartridge could be pre-loaded with a panel of cancer therapeutics (e.g., one each in an isolated chamber such as a well in a plate) and all the necessary tools for disaggregating and dispersing a sample into these wells.

The systems of the invention can include an internal imaging capability to address a module of a cartridge. This system can be used to generate data which is then outputted to a user or other device.

The analytical device can also include components necessary for thermal incubation to preserve cell viability while tests are run on the sample. The incubation portion of such an analytical device can hold one or more cartridges, optionally in a predetermined order (e.g., chronological order based on time of sample extraction).

Any of the foregoing devices that can also attach sample identifiers to modules of the cartridge and transmit sample information and process information via communication lines to other devices or can display a result for a user to examine.

C. Kits

The present invention is also directed to kits containing a device of the present invention. Example kits include one or more cartridges described herein packaged in a container. The kits can further include printed instructions for use, reagents and buffers, molecular probes, one or more test reagent as discussed below, disaggregation or distribution tools such as pipetters or needles, and other items useful in performing the methods described below.

In some embodiments, these kits can be sterilized using methods known in the art and packaged in a manner to preserve the sterilization. The kits can be sold as individual kits or in a multipacks. The kits can also be designed in a manner such that they are tamper resistant or designed to indicate if tampering has occurred.

A kit can include a cartridge for analysis as described herein that can be used manually rather than through the use of an automated apparatus. In such cases, reagents and equipment required to conduct the test or purpose of the cartridge can be provided as part of the kit. The equipment, e.g. syringes needles, pipettes, etc., may be preloaded onto the cartridge or may be outside of the cartridge and provided as part of the kit. In other embodiments, the equipment may be supplied by the user and not as part of the kit. Similarly, test reagents that are used with the kit may be preloaded into particular isolated chambers of the cartridge or packaged outside the cartridge for application by the used. Kits according to these embodiments can be packaged as, for example, a single cartridge for a single test, a single cartridge loaded or prepared for multiple tests, or multiple cartridges for multiple tests.

Optionally, the kit also contains directions for properly using the cartridge and other necessary items, e.g., reagents, as part of an assay or method such as those described herein. For example, the kit can contain a notice or printed instructions. Such printed instructions can be in a form prescribed by a governmental agency regulating the manufacture, use, or sale of pharmaceuticals or biological products, which notice reflects approval by the agency of the manufacture, use, or sale for human administration to diagnose or treat a condition that could be treated using information derived from the assays, methods, and devices described herein. In some embodiments, the kit further comprises printed matter, which, e.g., provides information on the use of the kit to process cells or a pre-recorded media device which, e.g., provides information on the use of the kit to process cells.

"Printed matter" can be, for example, one of a book, booklet, brochure or leaflet. The printed matter can describe experimental assays and/or protocols for processing cells according to the present methods. Possible formats include, but are not limited to, step-wise instructions, a bullet point list, a list of frequently asked questions (FAQ) or a chart. Additionally, the information to be imparted can be illustrated in non-textual terms using pictures, graphics, or other symbols.

"Pre-recorded media device" can be, for example, a visual media device, such as a videotape cassette, a DVD (digital video disk), filmstrip, 35 mm movie, or any other visual media device. Alternately, pre-recorded media device can be an interactive software application, such as a CD-ROM (compact disk-read only memory) or floppy disk. Alternately, pre-recorded media device can be, for example, an audio media device, such as a record, audiocassette, or audio compact disk. The information contained on the pre-recorded media device can describe experimental assays and/or protocols for processing cells according to the present methods.

II. Methods

The present invention is directed to novel methods of processing cellular samples, in particular aggregated cells or solid tumors which can be used in a clinical or research context. These methods include disaggregating and dispersing an aqueous solution containing live cancer cells obtained from a subject into at least one test aliquot in a first isolated chamber; optionally purifying or manipulating the sample to increase the percentage of target cells relative to other contaminating cell types by removing the contaminating cells; distributing the purified live cancer cells into one or more second isolated chambers for analysis, manipulation, or stimulation; and stabilizing the distributed live cells to permit cellular and/or molecular analysis of the distributed cells. In some embodiments, the stabilized and distributed cells can be live cells or dead cells, depending on the desired outcome and the cellular assay of interest.

Other methods of the present invention include methods for processing or preparing cancer cells from a solid tumor comprising: a. disaggregating and dispersing live cancer cells obtained from a solid tumor into at least one test aliquot in at least one first isolated chamber; optionally purifying or manipulating the live cancer cells to remove contaminants; distributing the purified live, purified cancer cells into one or more second isolated chambers for analysis; and stabilizing the distributed cells to permit cellular and/or molecular analysis of the cells.

Figure 17:
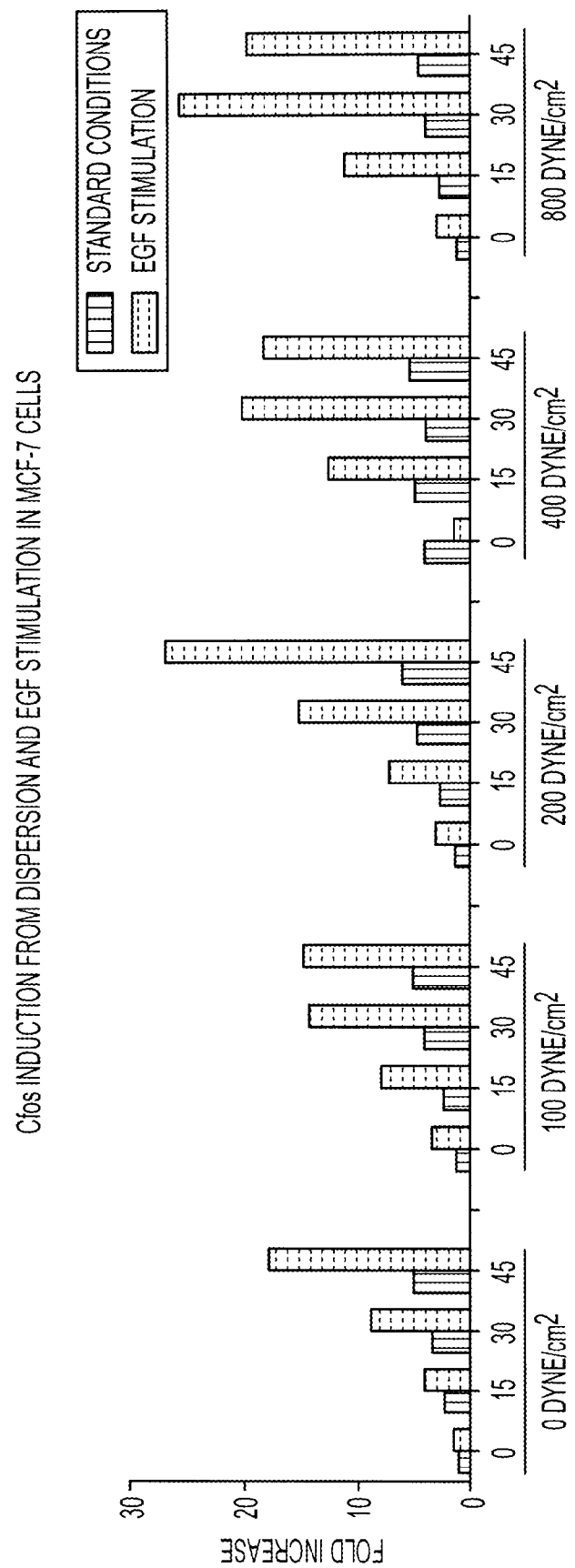
FIG. 17 shows varying levels of FOS induction from dispersion and EGF stimulation in MCF-7 cells.

The methods of the present invention allow live cells to be processed rapidly. The cells can be processed in a live state with minimal cellular activation or stress (e.g., environmental stress, temperature induced stress, metabolic stress, or chemically induced stress). The term "minimal cellular activation or stress" is defined by minimal changes in background noise of cell signaling and cell stress pathways compared to stimulation. For example, as seen in FIG. 17, a comparison of FOS (or c-fos) induction in cells before and after disaggregation and/or dispersion can show minimal induction (3-5 fold) of FOS or other early response genes or biological stress indicators compared to stimulated samples (20-30 fold increase).

Another advantage of the methods of the present invention is that they can use very low numbers of cells in the original sample. For example, in some embodiments the total number of aggregated cells or solid tumor cells processed is between about $1 \times 10^3$ and $1 \times 10^7$.

The methods of the present invention also allow for rapid sample processing. In some embodiments, the stabilization of the distributed live cells is completed within about one hour, about two hours, about three hours, or about four hours of obtaining the sample from the subject. This surprisingly short processing time eliminates the need for cell culturing while maintaining high rates of cell viability, for example, over about 50%, 60%, 70%, 75%, 80%, 85%, 90%, or 95%. In some embodiments, the rate of cell viability is about 70% or about 75%. The term "about" when used in conjunction with a number, for example a percentage, means plus or minus 10% of the number. For example, the term "about 60%" includes between 54% to 66%.

A. Obtaining the Sample

The sample used in the methods and devices described herein can be obtained in a variety of ways. The sample can be live cells taken from a subject, such as a mammal (e.g. a human) or another living organism. For example, the sample can be a biopsy taken from a human patient in a clinical setting for analysis which is eventually used to help determine the proper clinical diagnosis and course of treatment.

The sample in some embodiments can also be any group of cells or single cell, aggregated or disaggregated, that is of interest in a research or clinical setting. For example, solid tumors as well as individual cells such as lymphomas or cells that have been disaggregated using other means than described herein, such as, by using trypsin. These samples can be from existing cell lines, xenografts, or patient specimens that are examined for reasons other than to provide a clinical diagnosis. Such samples can be analyzed to further characterize the cells and their responses to specific test reagents. These applications can be useful as part of drug development and screening assays to identify new compounds or improve the administration of existing compounds.

In some embodiments, the methods described herein can be used with any type of aggregated cells or tumor cells. For example, they can test and process carcinomas or sarcomas. Example cancers that can be tested with the present methods include, but are not limited to, colon cancer, pancreatic cancer, breast cancer, ovarian cancer, prostate cancer, squamous cell carcinoma, cervical cancer, lung cancer, small cell lung carcinoma, kidney cancer, liver cancer, brain cancer, skin cancer, and bladder cancer. These cancers can be from a human, other mammal, or a xenograft of human cancer cells removed from a non-human mammal (e.g., a mouse).

In some embodiments, the tissue sample is a portion of a solid tumor or a complete tumor. Such a tissue sample containing tumor cells for use in the present invention may be obtained by any method as is know in the art, for example, by taking a biopsy from a patient. Suitable biopsies that may be employed in the present invention include, but are not limited to, incisional biopsies, core biopsies, punch biopsies and fine needle aspiration biopsies, as well as excisional biopsies. In some embodiments, the biopsy is obtained by fine needle aspiration (FNA) of a tumor.

Fine Needle Aspiration (FNA) biopsy is performed with a fine needle sometimes attached to a syringe and other times used independently. Aspiration biopsy or FNA may be employed in the present invention to obtain a cancer sample. FNA biopsy may be a percutaneous (through the skin) biopsy or alternatively through the lumen of an organ such as the bronchus, esophagus, stomach, or intestine. FNA biopsy is typically accomplished with a fine gauge needle (21 gauge or finer, e.g., 22 gauge or 25 gauge). The area is first cleansed and then usually numbed with a local anesthetic. The needle is placed into the region of organ or tissue of interest. Once the needle is placed a vacuum may be created with the syringe, or alternatively capillary action within the needle alone may be utilized, and multiple in and out needle motions are performed. The cells to be sampled are brought into the lumen of the needle and sometimes the hub of the needle through a micro-coring action of the bevel of the needle as it passes through the tissue. Three to six separate samples are usually made. Metastatic cancer sites such as lymph nodes and liver are good candidates for FNA biopsies. FNA procedures are typically done using ultrasound or computed tomography (CT) imaging.

A core needle biopsy (or core biopsy) is performed by inserting a small hollow needle through the skin and into the organ. The needle is then advanced within the cell layers to remove a sample or core. The needle may be designed with a cutting tip to help remove the sample of tissue. Core biopsy is often performed with the use of spring loaded gun to help remove the tissue sample. Core biopsy is typically performed under image guidance such as CT imaging, ultrasound or mammography. The needle is either placed by hand or with the assistance of a sampling device. Multiple insertions are often made to obtain sufficient tissue, and multiple samples are taken. Core biopsy is sometimes suction assisted with a vacuum device (vacuum assisted biopsy). This method enables the removal of multiple samples with only one needle insertion. Unlike core biopsy, the vacuum assisted biopsy probe is inserted just once into the tissue through a tiny skin nick. Multiple samples are then taken using a rotation of the sampling needle aperture (opening) and with the assistance of suction. Thus, core needle biopsy or vacuum assisted needle biopsy may be employed in the present invention to obtain a tissue sample.

Endoscopic biopsy is a common type of biopsy that may be employed in the present invention to obtain a sample. Endoscopic biopsy is done through an endoscope (a fiber optic cable for viewing inside the body) which is inserted into the body along with sampling instruments. The endoscope allows for direct visualization of an area on the lining of the organ of interest; and collection or pinching off of tiny bits of tissue with forceps attached to a long cable that runs inside the endoscope of the sample. Endoscopic biopsy may be performed on, for example, the gastrointestinal tract (alimentary tract endoscopy), urinary bladder (cystoscopy), abdominal cavity (laparoscopy), joint cavity (arthroscopy), mid-portion of the chest (mediastinoscopy), or trachea and bronchial system (laryngoscopy and bronchoscopy), either through a natural body orifice or a small surgical incision. Endoscopic ultrasound-guided fine needle aspiration biopsy may also be performed on lung or mediastinal lymph nodes, pancreas, or liver using a trans-esophageal, trans-gastric or trans-duodenal approach.

Surface biopsy may be employed in the present invention to obtain a cancer sample. This technique involves sampling or scraping of the surface of a tissue or organ to remove cells. Surface biopsy is often performed to remove a small piece of skin.

B. Cell Dispersion and Disaggregation

The sample obtained for processing can be prepared for analysis by separating the cells from one another (if aggregated) and then dispersing the separated cells into test aliquots within the cartridges described herein or into another suitable container. This process may consist of multiple steps including dispersion and counting/viability assays.

Compared to samples from surgically-excised tumors, the samples used in the methods of the present invention can contain relatively small numbers of cells (e.g., tumor cells), which, in the absence of the methods disclosed herein, can in some cases limit utilization of these small samples in many current molecular diagnostic technologies. Further, FNA samples from solid tumors or solid tumor cells obtained using other methods can contain extremely large clumps of cells (>500 cells), which prohibit uniform distribution of the specimen into multiple testing compartments.

Disaggregating and dispersing such cells while not killing or unduly activating stress response pathways within the cells is a delicate process that requires precise methods and techniques. As used herein, disaggregation means separating cells or providing an approximately homogeneous sample of cells in such a way that a sample containing the cells is capable of being dispersed into multiple relatively uniform samples. For example, in anchorage-dependent cells such as endothelium, sustained unidirectional laminar shear forces at arterial levels (10 to 25 dyne/cm$^2$) can cause rapid changes in metabolism (prostacyclin and NO production) as well as rapid changes in gene expression with FOS mRNA and FOS protein enhanced in less than an hour. Several other cell lines such as CHO and HELA also display FOS induction after sustained exposure to unidirectional shear stress. These studies typically deploy flow chambers where cells are exposed to shear stresses for minutes to hours to days to alter phenotype. See, e.g., Diamond S L, Eskin S G, McIntire L V. Fluid flow stimulates tissue plasminogen activator secretion by cultured human endothelial cells. Science. 1989 Mar. 17; 243(4897):1483-5. Distinct from fluid shear studies, mechanical perturbation (substrate stretching or induced deformation) can activate stretch-activated ion channels and can cause calcium mobilization. Turbulent shear stresses are typically more detrimental than laminar shear stresses in that interactions with collapsing films of bursting oxygen bubbles are particularly cytolytic. Additives such as pluronic F68 or bovine serum are cytoprotective, but partly act via surfactant effects that prevent cells from associating with air bubbles.

The present inventors have surprisingly found that using predetermined amounts of laminar fluid shear stress can effectively disrupt aggregates of cells without killing the cells and triggering only a minimal stress response or no stress response in the cells. This disaggregation can be done, for example, by drawing the cells into a needle or tube of a predetermined size and ejecting the cells, e.g. into a well, and repeating as necessary. The exposure time to laminar shear stress is minimized to reduce shear activation of cells during fluid mechanical disruptions of the specimens.

The proper conditions for disaggregation of a sample can be calculated to identify the equipment and protocol needed. The aggregation state at any instant of a cellular system is defined by its population size distribution. A system may be monodisperse (e.g. all singlets or aggregates containing small numbers of cells, for example all 20-mers or less) or polydisperse with aggregates ranging between singlets and a range of k-mers, where k is a large number greater than, for example, 20. In cell culture lines, aggregates are homotypic. However, FNAs are heterotypic in that they contain multiple cell types. The mathematics of aggregation and fragmentation processes that evolve in time are well developed. Depending on the complexity, population balance equations can be solved analytically (simple homotypic aggregation), numerically (complex homotypic aggregation), or by Monte Carlo simulation (heterotypic aggregation/fragmentation). For FNA disruption, the fundamental process is dictated by the fragmentation kernel F which depends on prevailing flow fields, aggregate size, and buffer conditions. For a population of sizes undergoing fragmentation (single component with each particle breaking into two smaller particles), the fragmentation balance may be expressed as:

$$\frac{dc_k(t)}{dt} = -c_k(t) \sum_{i=1}^{k-1} F_{i,k-i} + 2 \sum_{j=k+1}^{\infty} F_{k,j-k} c_j(t)$$

where $c_k(t)$ is the concentration of k-sized particles (or k-mers) at time t and $a_k$ is the net breakup rate of k-mers and $b_{i|k}$ is the average number of i-mers produced upon breakup of a k-mer. Thus, $F_{ij}=a_{i+j}b_{i|i+j}/2$ gives the net rate that (i+j)-mers break into i-mers and j-mers. The Fragmentation Kernal F is spatially dependent in tube flow (high near the wall, zero in the center) and is also dependent on the ratio of the aggregate size to the tube diameter. In the manipulations after biopsy, the FNAs will be highly dilute (cell volume/sample volume<<1) so that suspension dynamics involving radial migration to the walls of the smallest particles are not important. Fragmentation of an aggregate can range from binary fissure to pure ginding (loss of singlets from the aggregate). Fragmentation Kernals are not known for tumor aggregates in FNAs. As one of skill in the art will appreciate, empirical fragmentation rates for clusters in shear flow are power-law relationships based on the average shear rate $G_{avg}$ and the aggregate hydrodynamic radius or collision radius $R_{hyd}$. For example, a common form is: $a_i=A^*(G_{avg})^{\gamma}(R_{hyd})^{\gamma}$ with A and $\gamma$ determined experimentally and $\gamma=2$. For a tumor aggregate of i-cells where each cell has a radius $R_o$, then $R_{hyd}=R_o(i)^{1/Df}$ where $D_f$ is the fractal dimension ($D_f$~1.7 to 2.5).

FNAs, and other cell aggregates, can be complex objects with multiple cell types and various matrix constituents. In considering the disruption of FNAs, the fragmentation of the large tissue samples derived from the patient into a subpopulation is primarily an issue of disruption of junctions between tumor cells and secondarily disrupting integrin-dependent adhesion between the tumor cell and the underlying matrix.

Shear induced disaggregation of biopsy samples, e.g., FNAs, in tubes: One method of disaggregating cells is through the use of shear stress. As mentioned above, laminar shear stress is preferred. Laminar shear stress can be generated in tubes.

For laminar shear flow in a tube (Reynolds number<2100), the shear stresses are greatest near the tube wall and are zero in the center of the tube where fluid is simply translating downstream. Wall shear stress $t_w$ and transit time $t_{transit}$ may be defined as: $t_w$ (dyne/cm$^2$)=4 mQ/($\pi R^3$) and $t_{transit}$=(LA)/Q for volumetric flow rate Q though a tube of cross-sectional area A=$\pi R^2$ where: Q=$v_{avg}$A for Q[=]cm$^3$/s, $v_{avg}$[=]cm/s, and A[=]cm$^2$. The average transit time across a length of tubing L is defined from $v_{avg}$=L/$t_{transit}$ such that $t_{transit}$=L/$v_{avg}$=L A/Q. The viscosity of water is 0.01 Poise at room temperature. Additives such as glycerol, pluronic F68, dextran, polyethylene glycol (PEG) can all enhance the viscosity of the fluid phase. At constant flow rate and geometry, increasing the viscosity will increase the shear forces. Entrance length effects are fairly minimal in small diameter tubes. For a commonly used length of 1" syringe and syringe gauges (G) and water perfusion buffer (1 cP), wall shear stresses (dpc, dyne/cm$^2$) and transit times are given in Table 1.

TABLE 1

Relationship of needle gauge, wall shear stress (dpc, dynes/cm$^2$), and transit time (msec) for 1" needle perfused with water buffer at 1 mL/s (viscosity = 1 cP).

| Needle Gauge | ID inches | Radius cm | Area cm$^2$ | Shear Stress (dpic) Q = 1.0 mL/s | Avg. Velocity (mils) Q = 1.0 mL/s | Transit Time Onsec) 1-in. syringe (Q = 1.0 mL/s) |
|---|---|---|---|---|---|---|
| 10 | 0.109 | 1.346E-01 | 5.693E-02 | 5.219 | 17.58 | 144.6115 |
| 11 | 0.094 | 1.194E-01 | 4.477E-02 | 7.484 | 22.34 | 113.7226 |
| 12 | 0.085 | 1.080E-01 | 3.661E-02 | 10.121 | 27.32 | 92.9884 |
| 13 | 0.071 | 9.017E-02 | 2.554E-02 | 17.367 | 39.15 | 64.8795 |
| 14 | 0.063 | 8.001E-02 | 2.011E-02 | 24.859 | 49.72 | 51.0825 |
| 15 | 0.054 | 6.858E-02 | 1.478E-02 | 39.475 | 67.86 | 37.5300 |
| 18 | 0.047 | 5.969E-02 | 1.119E-02 | 59.870 | 89.34 | 28.4306 |
| 17 | 0.042 | 5.334E-02 | 8.938E-03 | 83.898 | 111.88 | 22.7033 |
| 18 | 0.033 | 4.191E-02 | 5.518E-03 | 172.965 | 181.22 | 14.0158 |
| 19 | 0.027 | 3.429E-02 | 3.694E-03 | 315.797 | 270.72 | 9.3825 |
| 20 | 0.023 | 2.921E-02 | 2.680E-03 | 510.876 | 373.07 | 6.8084 |
| 21 | 0.0195 | 2.477E-02 | 1.927E-03 | 839.292 | 519.01 | 4.940 |
| 22 | 0.0155 | 1.969E-02 | 1.217E-03 | 1669.184 | 821.45 | 3.0921 |
| 23 | 0.0125 | 1.588E-02 | 7.917E-04 | 3182.506 | 1263.06 | 2.0110 |
| 24 | 0.0115 | 1.461E-02 | 6.701E-04 | 4087.011 | 1492.27 | 1.7021 |

TABLE 1-continued

Relationship of needle gauge, wall shear stress (dpc, dynes/cm$^2$), and transit time (msec) for 1" needle perfused with water buffer at 1 mL/s (viscosity = 1 cP).

| Needle Gauge | ID inches | Radius cm | Area cm$^2$ | Shear Stress (dpic) Q = 1.0 mL/s | Avg. Velocity (mils) Q = 1.0 mL/s | Transit Time Onsec) 1-in. syringe (Q = 1.0 mL/s) |
|---|---|---|---|---|---|---|
| 25 | 0.0095 | 1.207E−02 | 4.573E−04 | 7249.841 | 2186.73 | 1.1616 |
| 28 | 0.0095 | 1.207E−02 | 4.573E−04 | 7249.841 | 2186.73 | 1.1616 |
| 27 | 0.0075 | 9.525E−03 | 2.850E−04 | 14733.826 | 35138.49 | 0.7240 |
| 28 | 0.0065 | 8.255E−03 | 2.141E−04 | 22633.893 | 4671.07 | 0.5438 |
| 29 | 0.0065 | 8.255E−03 | 2.141E−04 | 22633.893 | 4671.07 | 0.5438 |
| 30 | 0.0055 | 6.985E−03 | 1.533E−04 | 37360.377 | 6524.05 | 0.3893 |
| 31 | 0.0045 | 5.715E−03 | 1.026E−04 | 68212.157 | 9745.80 | 0.2606 |
| 32 | 0.0035 | 4.445E−93 | 6.207E−05 | 144975.692 | 16110.41 | 0.1577 |
| 33 | 0.0035 | 4.445E−03 | 6.207E−05 | 144975.692 | 16110.41 | 0.1577 |

Laminar tube flow is one example of moderate extensional flow. Impinging flows such as a tube directed at a nearby flat surface are highly extensional. The cellular suspension experiences the extensional forces for fleeting periods of time at the exit of the tube before entering a low shear environment. The magnitude of the extensional forces are easily controlled by tube diameter, flow rate, and distances from the flat surface. Routine motion control and micromanipulation can control distances with an accuracy within 10 microns. Also, entrance of fluid into a needle or exit of fluid from a needle can create strong elongational flows. By use of varying lengths and inner diameters (Gauge), it is possible to distinguish disaggregation due to wall shear stress exposure from that cause by entrance or exit into the needle.

Based on the calculated force and equipment needed, the cells of the tissue sample can be passed through a tube having a diameter of 10 to 500 microns using volumes between 10 and 2000 microliters to create wall shear stresses of 100-800 dyne/cm$^2$. In some embodiments, the cells are passed through a 22 gauge or 18 gauge needle. In some embodiments, the cells are exposed to laminar wall shear stresses of about 100 to about 800 dyne/cm$^2$, laminar wall shear stresses of about 300-about 500 dyne/cm$^2$; or laminar wall shear stresses of about 350-about 450 dyne/cm$^2$. The cells can be exposed to the laminar wall shear stress for between about 10 msec to about 500 msec or longer, depending on the amount of force needed and the type of cell.

In some embodiments, the viscosity of the media is adjusted, in order to provide the proper shear force.

The disaggregation step can be repeated as necessary until a suitable sample for analysis has been produced. In some embodiments, at least about 70%, about 80%, about 90%, or more than about 90% of the cells are dispersed into clumps of 1-100 cells. The clumps can also be groups of 5-100 cells, 10-100 cells, 10-25 cells, or 5-25 cells. Preferably the clumps have fewer than 15 cells, for example, 1-10 cells per clump.

The disaggregation step can also involve adding a compound to aid in disaggregation or to prevent activation of a stress response in the cells. For example, any of the following can be added to the cells during the disaggregation step a physiologically acceptable antioxidant; a mucolytic agent; an agent capable of reducing disulfide bonds, e.g., N-acetyl-L-cysteine or dithiothreitol; a physiologically acceptable chelating agent, e.g., EDTA; and/or one or more membrane-protecting surface active agent such as a nonionic surfactant, e.g. polyethylene glycol, a polyethoxylated fatty acid, or an ethylenoxide and propylenoxide block copolymer, for example Pluronic F-68 (BASF).

The dispersion process can also involve suspending the cells or clumps of cells in a serum-free isotonic saline solution, e.g., about 0.9% w/v sodium chloride in sterile water, optionally further comprising physiologically acceptable buffers and salts; e.g., a saline solution selected from lactated Ringer's solution, acetated Ringer's solution, phosphate buffered saline, TRIS-buffered saline, Hank's balanced salt solution, Earle's balanced salt solution, standard saline citrate, HEPES-buffered saline.

As one of skill in the art will appreciate, the cellular disaggregation process can be done manually, for example by a person using a pipetter or a needle, or by using an automated process such as an air or fluid driven automated fluidic processing device. Both manual and automated disaggregation processes are encompassed by the various embodiments of the present invention.

In some embodiments, the tissue sample is disaggregated and dispersed while response pathways, including but not limited to cellular signal transduction and stress response pathways, are not activated in comparison to ligand stimulation, for example wherein the dispersion does not activate FOS expression in comparison to EGF stimulation.

C. Sample Purification/Enrichment

Aggregated cells can be composed of multiple cell types and often only very few or one of those cell types is the target for examination and analysis. In these cases, the cells can be disaggregated into smaller clumps and/or individual cells and then the mixture is purified to remove contaminants, including cells that are not of interest, to purify the sample and enrich it by providing a higher percentage of the cells of interest than in the original mixed cellular sample. As used herein, "purify" or "enrich" means to increase the ratio of the number of target cells (e.g., tumor cells or other cell being analyzed) to the number of non-target cells or parts of cells that might otherwise interfere with analysis.

For example, biopsy specimens from solid tumors are composed of a mixture of cells including both the cells of interest (e.g. tumor cells) and contaminating normal cellular elements (hematopoietic cells, hepatocytes, vasculature, etc). In an exemplary embodiment, the contaminating elements are removed using antibodies specific to the contaminating elements or by using antibodies specific to the target cells, depending on the protocol. The antibodies may be bound to a substrate, for example, a plastic surface, e.g., the wall of a plate, or plastic or plastic-coated beads, e.g., magnetic beads, either directly, or through a second antibody recognizing the first antibody, so as to remove the contaminating materials from the cells of interest.

D. Distributing the Cells

Once the cells have been disaggregated and optionally purified (only if necessary), the sample of cells is distributed into one or more isolated chambers (e.g., one or more of the second isolated chambers discussed above) within a cartridge of the present invention or another suitable container.

The cells of interest may if desired be further dispersed using techniques as described in B above, and then they are distributed into aliquots for exposure to test reagents and/or other analysis and testing. In some embodiments, the aliquots are distributed among some or all of the wells in a customized cartridge. The aliquots are exposed to desired test reagents, for example to one or more ligands to stimulate cell proliferation, and signal transduction.

The aliquot distributed to the second isolated chamber or other substrate for testing can vary depending on the number of cells needed and other experimental conditions known to one of skill in the art. In some embodiments, the test aliquot has a volume of less than 2 mL, less than 200 µL, or between 1 µl and 200 µL. As one of skill in the art will appreciate, the volume can be varied outside these example ranges if needed so long as a suitable number of cells are available in the suspension for testing.

In some embodiments, at least one isolated chamber that has received a test aliquot is designated as a control. This control can be reassayed for viability and level of stress, undergo cellular counting processes, or receive additional reagents or control substances to provide a positive or negative control for data analysis of the other chambers.

The distributed cells can be suspended in any medium that is suitable for the cell type. For example, the test aliquots of distributed cells can be in a serum-free minimal nutrient medium. The serum-free minimal nutrient medium can have essential amino acids, salts (e.g., potassium chloride, magnesium sulfate, sodium chloride, and sodium dihydrogen phosphate), glucose and vitamins (e.g. folic acid, nicotinamide, riboflavin, B-12); and any other component necessary for proper processing or analysis of the cells. Suitable serum-free nutrient mediums include Dulbecco/Vogt modified Eagle's minimal essential medium (DMEM) or RPMI.

In some embodiments, the test aliquots are distributed into wells in a plastic plate, e.g., a 96 well plate, wherein the walls of the wells are coated with a physiologically acceptable hydrogel or oil, e.g., polyethylene glycol, dextran, alginate, or silicone.

E. Test Reagents and Testing

The test aliquots can be exposed to a variety of test reagents either in the cartridge or after separating one or more of the isolated chambers form the cartridge. An advantage of the methods and devices herein is that the test reagent can be added at the point of care and/or can come preloaded in specified wells of the cartridge. This allows the testing of ex vivo biomarkers, optionally at the point of care, using live cells. These methods and devices can be used with specific test reagents to manipulate samples ex vivo to facilitate the development of novel predictive biomarkers, monitor and determine cellular sensitivity to specific pharmaceutical agents, and other uses that one of skill in the art will appreciate.

For example, a sample of a solid tumor from a patient can be disaggregated, distributed, and then tested against a panel of currently available cancer therapeutics at the point of care. The samples can then be stabilized and/or fixed if necessary and analyzed. Depending on the results for each test reagent, the physician can quickly determine which therapeutics will be most effective on the individual patient's tumor at the point of care. This personalized medicine provides numerous benefits, in particular, the use of targeted cancer therapeutics and regimens in a rapid, cost effective manner.

Embodiments of the invention are directed to analyzing the distributed cells (e.g., cancer cells) by administering at least one agent to produce a measurable quantitative or qualitative effect on a target ex vivo biomarker or biomolecule. The quantitative or qualitative effect can be the activation or inhibition of a cellular pathway. Exemplary cellular pathways include, but are not limited to, a metabolic pathway, a replication pathway, a cellular signaling pathway, an oncogenic signaling pathway, an apoptotic pathway, and a pro-angiogenic pathway. For example, the quantitative or qualitative effect can be a measurement of an agonistic or antagonistic effect on a G-protein coupled receptor or a receptor tyrosine kinase, such as, epidermal growth factor receptor (EGFR) and the downstream pathways.

The quantitative or qualitative effect measured can be the expression level of a gene, such as, an immediate or delayed early gene family member. Suitable immediate or delayed early gene family members include, but are not limited to, FOS, JUN and DUSP 1-28.

The effects of the presence or absence of a test reagent can also be determined by detecting an ex vivo biomarker, for example, a post-translationally modified protein, ions, or enzymes.

Suitable test reagents can include, but are not limited to, one or more of the following: a pharmaceutical agent, a chemical compound, an agent for stimulating a cell, a polypeptide, a polynucleotide, an antibody, an Fab fragment, an Fc fragment, RNA, miRNA, siRNA and a phosphoprotein. As discussed above, the administration of a reagent can be followed by measuring a quantitative or qualitative effect on a target ex vivo biomarker or biomolecule of the dispersed or distributed cell.

For certain analytical methods, the test reagent can be a detectable agent. The detectable agent can be used individually or as conjugated or otherwise connected to another compound (e.g., a detectable agent conjugated to an antibody). Suitable detectable agents include, but are not limited to, an enzyme, fluorescent material, luminescent material, bioluminescent material, radioactive material, positron emitting metal using a positron emission tomography, or a nonradioactive paramagnetic metal ion.

Other suitable test reagents include tumor-cell stimulatory ligands, such as, a growth factor (e.g. EGF, insulin, VEGF), or a hormone, e.g., estrogen or an estrogenic compound.

For solid tumor or other cancer applications of the present methods and devices, the test reagents can include a targeted pharmaceutical agent such as, for example, antitumor monoclonal antibodies, e.g. trastuzumab (Herceptin®), cetuximab (Erbitux®), bevacizumab (Avastin®) and rituximab (Rituxan®& or Mabthera®), and small molecule inhibitors e.g., gefitinib (Iressa®), or erlotinib (Tarceva®) or cytotoxic chemotherapy agents, such as, for example taxanes (Taxotere®), antimetabolites (fluorouracil), alkylating agents, platinum agents or anthracyclines. These exemplary pharmaceutical agents can be used individually, in any combination with another pharmaceutical agent disclosed herein, or in combination with another compound.

After administering a test reagent, it can be determined if the test reagent affects the expression of one or more markers, wherein the presence, absence, or relative degree of such expression is indicative of the susceptibility of the cells to a selected pharmaceutical agent. These markers can include a wide array of ex vivo biomarkers such as mRNA, a microRNA, cDNA, a protein, a phosphoprotein, a posttranslational modification of a protein, or a modification of histone or DNA packaging. For example, the marker can be mRNA or cDNA for an early response gene (e.g., FOS or JUN) associated with susceptibility to a pharmaceutical agent. The presence, absence, or relative degree of expression of combinations of markers in the presence of a test reagent can be indicative of the susceptibility of the cells to a selected test reagent, such as a pharmaceutical agent.

F. Sample Preparation and Stabilization

As described herein and illustrated in the figures, the cells processed using the present invention can be prepared and stabilized in a number of ways to permit a wide array of cellular analyses to be performed on them. For example, the cells can be prepared for nucleic acid analysis, protein analysis, and/or analyzed using live cellular probes.

For nucleic acid analysis, a stabilizing reagent such as RNAlater®, RNA Protect Cell Reagent® (both available from Qiagen), or ethanol can be added to the cells. The stabilized cells can then be optionally lysed or have the nucleic acid of interest otherwise extracted. The extracted and purified nucleic acid can then be analyzed, for example, using PCR techniques.

In some embodiments, and as described above, the methods described herein yield nucleic acids for further analysis. For these samples, following dispersion and optional enrichment, the nucleic acids can be stabilized or extracted (optionally) to yield high quality and quantity nucleic acids. See, for example, Example 10 below and FIGS. 13 and 14. This can be done, for example, by lysing the desired cells following exposure to a test reagent and then obtaining cDNA using reverse transcriptase and DNA primers. The DNA primers can comprise nonspecific primer complementary to poly A, e.g. oligo $(dT)_{12-18}$ or a specific primer complementary to a mRNA transcript of interest. As one of skill in the art will appreciate, the cells can be lysed using a variety of methods, such as, chemical or mechanical means.

Optionally, the cells can be stabilized with reagents to detect and/or preserve biomarker information, e.g., using reverse transcriptase and DNA primer to obtain cDNA transcripts, preparing RNA, DNA and protein for down stream molecular analysis.

For protein analysis, either whole cells or lysed cells can be used. Intact whole cells can be fixed and stabilized with a polymer, such as the one in Table 2 below, so that the sample adheres to the isolated chamber, for example, a glass slide. These samples can then be subjected to analysis, for example, immunohistochemical (IHC) analysis. Lysed or otherwise ruptured cells can be used in assays such as Western Blots and may not require stabilization or fixation.

Slide preparation for morphological review by a pathologist and protein analysis by IHC can be an output of the methods described herein. Accordingly, the cells can also be prepared, optionally using polymers, on glass slides for analysis of morphology and/or immunohistochemistry. For example, the mixture disclosed in Table 2 can be used according to the example protocol in Table 3. See also Maksem, J. A., V. Dhanwada, et al. (2006). "Testing automated liquid-based cytology samples with a manual liquid-based cytology method using residual cell suspensions from 500 ThinPrep cases." Diagn. Cytopathol 34(6): 391-6).

TABLE 2

| Polymer solution | |
|---|---|
| Agarose | 0.18 g |
| PEG | 4.8 g |
| Alcohol Reagent | 76.8 ml |
| Poly L-lysine (0.1%) | 0.25 ml |
| Nonidet P40**** | 0.05 mL |
| Total | 240 mL |

TABLE 3

| Example Protocol |
|---|
| 1 Dissolve 4.8 g of PEG in 15 ml of deionized water, heat up while stirring |
| 2 Dissolve 0.18 g of agarose in 15 ml of deionized water by heating the solution to boiling |
| 3 while maintaining vigorous mixing until the solution optically clears |
| 4 Immediately add the hot agarose solution to the PEG solution |
| 5 Dilute the solution with 133.2 ml of water (hot) and cool to room temperature |
| 6 Add 76.8 ml of reagent alcohol to the solution with mixing |
| 7 Adjust the final volume to 240 ml with deionized water |
| 8 Add 250 ul of poly-L-lysine solution |
| 9 Add 50 ul of IGEPAL CA-630 |
| 10 filter with cheese cloth, store at room temperature for at least 72 hr before use |

Live cellular probe analysis can involve adding a molecular probe (such as MitoTracker® as described in the examples) at any point in the method of processing the cells where the cells are alive. This addition of the live cell probe should be made prior to fixing or otherwise allowing the cells to die. For example, such a probe can be added before or after cellular stabilization but prior to cellular fixation.

In some embodiments, the cells can be stabilized and fixed by any suitable means that will permit subsequent molecular analysis and detection of markers. Generally, crosslinking fixatives such as formalin are not preferred but may be present in small amounts that will not interfere with subsequent analysis. Where the biomarker is expression of a particular gene or genes, in one embodiment the cells are lysed and exposed to reverse transcriptase and suitable primers, so as to generate cDNA transcripts of mRNA transcripts in the cells. This facilitates subsequent analysis, as cDNA is less subject to degradation than mRNA.

In some embodiments, $1 \times 10^4$ or more cells are processed to stabilize any or all of the following: RNA, DNA, protein, and/or phosphoproteins.

In some embodiments, the cells can be fixed after processing. Any suitable means of fixation can be used, for example, air drying techniques, adding a compound such as alcohol, e.g., a fixative comprising a lower alkanol, e.g. methanol or ethanol, adding formalin, adding an RNase inhibitor, adding agarose, adding polyethylene glycol, adding poly 1-lysine, or adding one or more chelator or antioxidant. In some embodiments, the fixative comprises agarose, polyethylene glycol, octylphenoxy-polyethylene glycol, poly-1-lysine, reagent alcohol and water.

A further embodiment of the methods of the present invention includes a method for preparing solid tissue cells from a subject, e.g., solid tumor cells from an animal or human subject having a solid tumor, e.g., for determination of sensitivity of the cells to a selected targeted pharmaceutical agent. An example method can include the steps of: (a) obtaining solid tissue comprising desired cells from the subject; (b) dispersing (e.g., using shear forces) the tissue into single live cells and/or aggregates of not more than 100 live cells, e.g., 10 to 100 cells; (c) enriching the sample, e.g. removing contaminating materials from the live cells; (d) distributing the live cells into test aliquots in isolated chambers; (e) exposing the live cells to one or more test reagents; and (f) treating the cells with a fixative and/or stabilizing agent (e.g., an agent stabilizing RNA, DNA, proteins and/or phosphoproteins) to fix the tumor cells and/or marker for further analysis; wherein the fixation of the tumor cells and/or the marker is completed within four hours of removal of the tissue from the subject in an automated or manual fashion.

Another embodiment the invention provides a method of testing cells wherein solid tumor cells are removed from a mammal (e.g., a human patient), and while most of the cells, e.g., at least 65% of the cells, e.g., at least 75% of the cells are viable and have not replicated outside the body, exposing all or a portion of the cells ex vivo to one or more test reagents, and stabilizing the cells, optionally with a fixative (e.g., a polymer) that can preserve biomarker information including cellular DNA, RNA, proteins, and/or phosphoproteins. These biomarkers can be tested using molecular analyses known to one of skill in the art or using the novel ex vivo biomarker tests disclosed herein.

The following examples are further illustrative of the present invention, but are not to be construed to limit the scope of the present invention.

Example 1

Live Cell Processing

The importance of live cell processing has been demonstrated using the live cell molecular probe, MitoTracker (available from Invitrogen, Carlsbad, Calif.). MitoTracker localizes to mitochondria when applied to living cells by passive diffusion across the plasma membrane. The living cells were fixed to stabilize the MitoTracker localization and analyzed by fluorescence microscopy. Unlike currently available biopsy processing methods utilizing methods, devices and systems according to the present invention enables the study of live cells with molecular probes. This is illustrated in FIGS. 20 and 21, where the specific cytoplasmic localization of mitochondria (granular fluorescence, left side—20A and 21A) was clearly demonstrated when the probe is applied to live cells, but was uninformative when applied to cells that were fixed using prior art methods (right side, 20B and 21B).

Example 2

MCF-7 and HCT-116 Dissaggregation Studies

MCF-7 (human breast carcinoma cells—ATCC#HTB-22) and HCT-116 (human colon carcinoma cells—ATCC#CCL-247) were used to examine the impact of shear forces on cluster size, viability and cellular activation in a semi-automated pipetting device. Briefly, MCF-7 and HCT-116 cells were grown to 80% confluency in tissue culture then removed from the plates by gently scraping with a rubber policeman and suspended in growth medium to mimic the cell number and fragment size in a typical FNA sample. One aliquot of the cell suspension was passed through an automated pipetting apparatus (Harvard Pipetter, Harvard Apparatus, Holliston, Mass.) with an 22 G needle four times (withdraw/infuse at 4.14 mL/min for each pass) resulting in a wall shear stress exposure ranging from 100-800 dyne/cm$^2$ and a total exposure time for each cell or aggregate of 4 transits×14 msec/transit=56 msec. Representative samples from each were cytocentrifuged onto a glass slide, fixed with 95% ethanol and stained with the Papanicolaou stain. Photomicrographs of representative areas were obtained (Magnification ×200). Note the decreasing cell cluster size with increasing shear forces. These results are illustrated in FIG. 22.

Example 3

Aggregation Size Distribution

Figure 15:
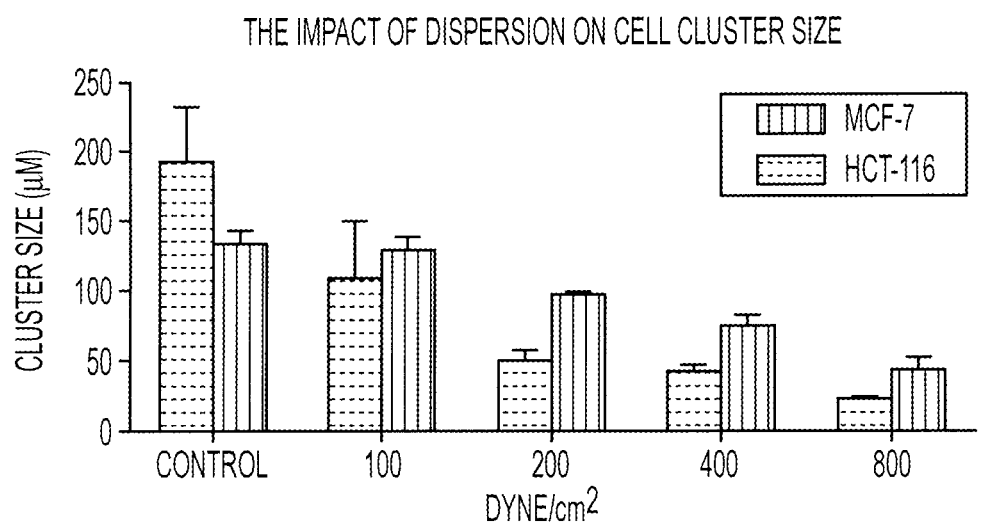
FIG. 15 shows the impact of dispersion at varying dyne/$cm^2$ on cluster size in MCF-7 and HCT-116 cells.

After using the method of example 2, average cluster size was then quantified through the use of a non-flow imaging-based cell counter that measures cell concentration and cell size distributions (Cellometer®, Nexcelom, Lawrence, Mass.). At 100 dyne/cm$^2$ the average cluster size of MCF-7 cells was 97±3 µm and HCT cells was 51±6 µm (FIG. 15). These data provide a range of reproducible, optimal shear forces necessary to disperse aggregates of live cells.

Example 4

Viability Analysis from Dispersion

Figure 16:
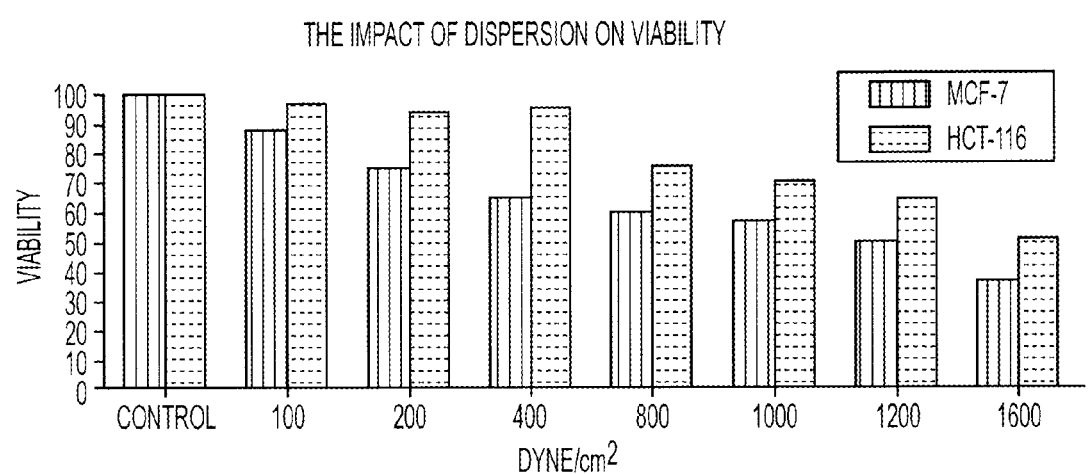
FIG. 16 shows the impact of dispersion at varying dyne/$cm^2$ on cell viability in MCF-7 and HCT-116 cells.

After using the method of example 2, viability was also examined by trypan blue exclusion assay at comparable shear forces from the semi-automated pipetter. It was concluded that shear forces greater than 800 dyne/cm$^2$ resulted in more than a 40% decrease in viability deemed too severe for live cell manipulations and processing. See FIG. 16 for a graphical depiction of the results obtained.

Example 5

Activation Analysis from Dispersion

Figure 18:
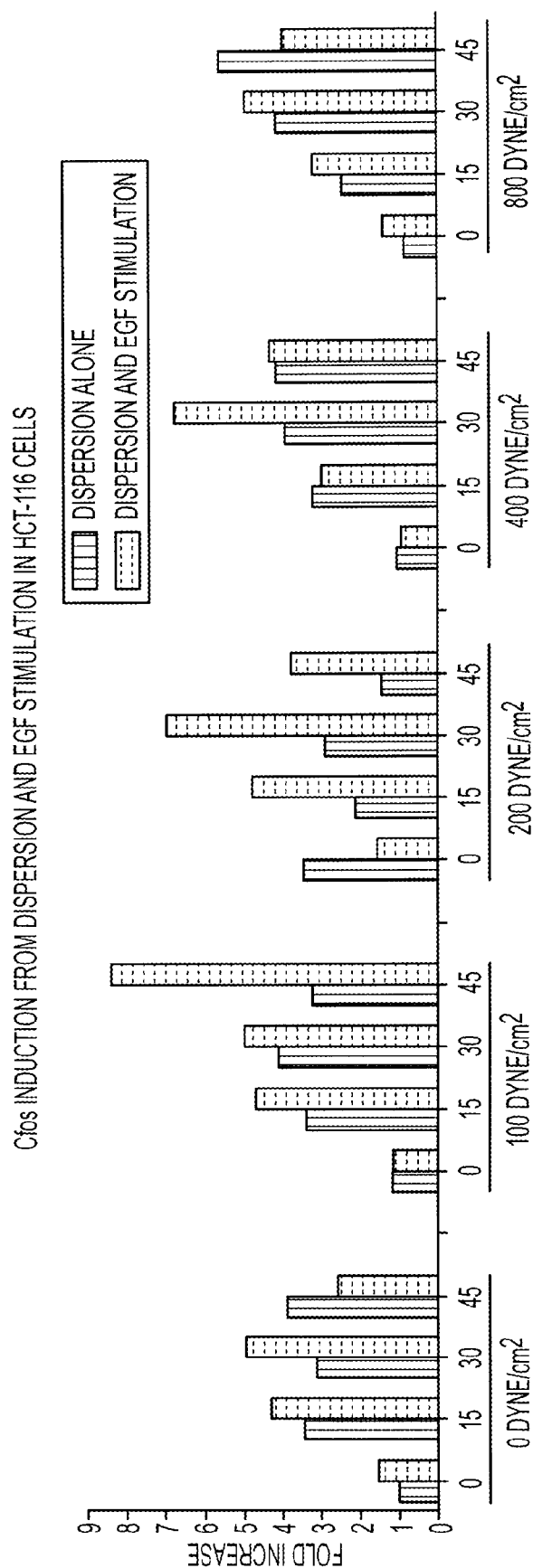
FIG. 18 shows varying levels of FOS induction from dispersion and EGF stimulation in HCT-116 cells.
Figure 19:
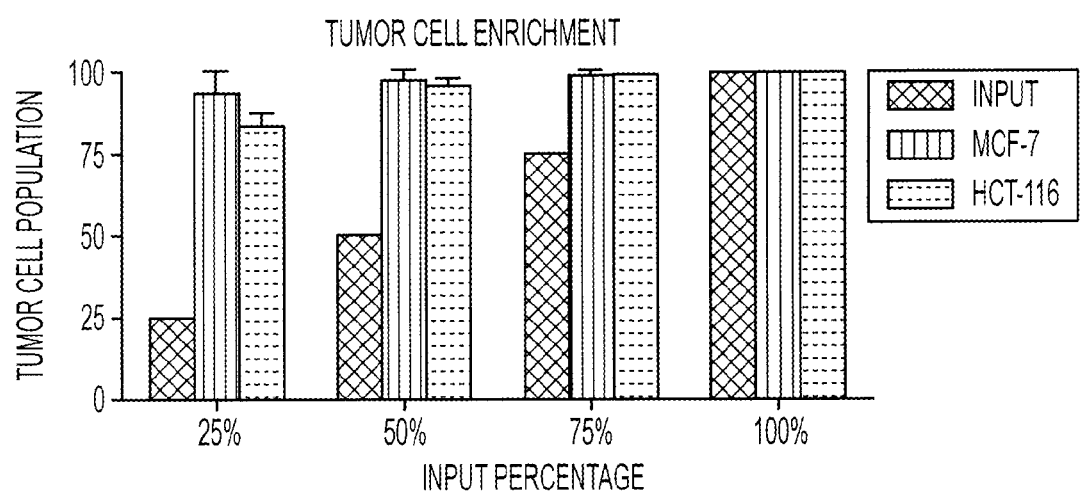
FIG. 19 shows tumor cell enrichment in MCF-7 and HCT-116 cells using the methods of the present invention.

A functional measurement of cellular activation includes FOS mRNA induction determined by quantitative RT-PCR. FOS is an early response gene associated with the EGFR pathway. In an experiment, MCF-7 cells were grown in normal growth conditions in 6 well plates to 80% confluency. Cells were gently scraped and exposed to increasing shear forces (0-800 dyne/cm$^2$ through the Harvard Pipetter) in addition to increasing incubation times (0-45 minutes) in the presence or absence of 100 ng/ml of EGF ligand (Sigma) prior to RNA extraction. FOS mRNA induction peaks at 30-45 minutes and returns to basal levels in approximately 60 minutes. FOS induction is also stimulated as a result of incubation with EGF ligand. Importantly, preliminary results indicate shear forces generated on a semi-automated platform of 100-800 dyne/cm$^2$ dispersion do not result in significant cellular activation compared to EGF stimulus. See FIGS. 17 and 18 for a graphical depiction of the results obtained.

Example 6

Apparatus

FIG. 1 shows a schematic view of an example cartridge for use, for example, in an apparatus, which provides a platform to integrate the function of conducting disaggregation of tissue, the function of cell-counter, the function of gene expression drug susceptibility testing, and the function of fixing a sample for further analysis. FIGS. 1-22 illustrate particular embodiments of features described herein. Persons skilled in the art will recognize how the various embodiments operate when the Figures are considered in conjunction with the present description.

The apparatus comprises as its main components: a storage cartridge 1, which can be inserted into an apparatus or used for manual processing, the cartridge having a plurality of small containers in, for example, a 96-well plate format 2 removable mounted on the cartridge, and a plurality of containers 3 for initial receipt, dispersion and removal of contaminating materials from the samples. The containers 3 may serve different functions, as depicted schematically in FIG. 2 and previously described herein. The cartridge has a label 4, which may be bar coded to facilitate identification of the sample. Each of the containers comprises a well and a seal that ensures biologic confinement of the contents and is puncturable by a needle, but resealable upon removal of the needle. A tissue sample is gathered from a patient, typically an aspiration biopsy using a fine needle 5 by a physician, who deposits the sample tissue into the receiver container 3 on the cartridge 1.

The cartridge 1 is then slid into the apparatus and closing door seals the apparatus, so that the cartridge 1 is biologically sealed from the outside environment and sealed against release of any of the biologically hazardous tissue sample. In an alternative embodiment, the cartridge is a platform containing particular reagents and can be processed manually.

The cartridge 1 can have one or more receptacles 6 for storage and disposal of raw materials for use in conducting the manipulation of the tissue sample. These raw materials include needle heads and reagents. The needle head consists of a needle having an aperture and a point and an annulus within the needle in fluid connection with the aperture and a syringe. The apparatus is self-contained with the exception of electric current, which can be supplied via cord if necessary.

The cartridges can include a receiver container 2 that houses a processing assembly, typically for mixing the tissue specimen therein. The receiver container 3 is prepackaged with a disaggregation solution of buffered saline; optionally further comprising chelators, antioxidants, and viscosity modifiers, with the constraint that the disaggregation solution should avoid the use of proteases.

The receiver container 3 consists of a seal cover for the well. This self-contained well and processing assembly arrangement minimizes human operator exposure to biohazards. An engagement extension protrudes through the seal cover.

The apparatus is fitted with an operator member, able to selectively pick up a needle head from storage well 6 on cartridge 1, to operate a syringe of the needle head, and to operate certain devices in the apparatus, such as the processing assembly on receiver container.

In the first operation within apparatus, the operator member retrieves a needle head from the storage well 6, moves to a position relative to the receiver container 3 in which the sample tissue has been deposited by the physician and which is prepackaged with a disaggregation solution, such buffers, chelators and antioxidant, punctures the seal on the receiver container 3 with the needle head and submerses the needle head point in the homogeneous solution mixture, withdraws a portion of the sample from the receiver container 3 into the syringe of the needle head, moves the needle head point to predetermined position within the receiver container and dispenses the withdrawn sample in the same or second receiver container 3 to disaggregate the tissue sample into a homogeneous solution of intact tumor cells and contaminant materials. This step is repeated as many times as necessary to achieve the predetermined level of disaggregation of the tissue sample. See, FIG. 3, e.g., 309.

The operator member (or operator if manually manipulated) retrieves a new needle head from the cartridge storage well 6, moves to a position relative to the receiver containers 3, punctures the seal on selected receiver container 3 with the needle head and submerses the needle head point in the homogeneous solution mixture, withdraws a portion of the sample from the receiver container into the syringe of the needle head, removes the needle from the receiver container, moves to a position relative to a matrix container, punctures the seal on the matrix container with the needle head and deposits the sample portion from the syringe into the matrix container 3. See also FIG. 2. The matrix container 3 consists of a loading chamber located above a bed of resin beads which is supported above a collection chamber at the bottom of the matrix container. The bed of resin is fitted with a plug that extends from the top surface of the bed to the bottom surface of the bed. The plug is constructed of material that permits puncturing by a needle head at the top surface of bed and permits the needle to extend through the bottom surface and into the collection chamber. See also FIG. 2. Alternatively, the bed of resin is fitted with a conduit extending from near the top of the loading chamber through the bed of resin to near the bottom of the collection chamber. In operation, the deposited sample solution would be deposited above the resin bed, would gravity feed and also be drawn though the bed of resin which removes the contaminants from the solution and collects in the collection chamber. The top of the conduit is situated so as to prevent any solution from bypassing the resin bed before collecting in the collection chamber.

In one embodiment, the sample is checked to ensure adequate numbers of cells dispersed in the sample. The operator member retrieves a needle head from the cartridge storage well 6, moves to a position relative to the receiver container, punctures the seal on the receiver container with the needle head and submerses the needle head point in the homogeneous solution mixture, withdraws a predetermined portion of the sample from the receiver container 3 into the syringe of the needle head, removes the needle head from the receiver container 3, moves to a position relative to a cell counter module and deposits the predetermined portion of the sample in the counter module. The needle head is then withdrawn from the counter container and disposed of in a disposal container on the cartridge.

The counter module, which may be one of the receiver modules 3 on the cartridge, is prepackaged with a dry dye on the interior of the holding chamber of the counter container. Within the counter container, the counter sample portion that has been deposited in the holding chamber dissolves the dye, which in turn stains the tumor cells. The predetermined sample portion funnels down into the counter tube, which is optically scanned for cell count by a scanner. The counter sample portion collects below the counter tube in a holding well. The optical scanner relays the count to an indicator that determines whether the count meets or exceeds the predetermined count size indicating a successful biopsy sample. The results of the analysis can then be displayed on a display and/or printed by a printer. The results then immediately guide the physician as to whether an additional biopsy is necessary. Provided the sample is adequate, the patient is excused.

Once the cells are dispersed and contaminants removed, the cells are divided into aliquots to be placed in a test matrix 2, typically a 96 well plate format. Typically, the wells have been prefilled with the desired media (buffered saline solution and test reagents). The operator member picks up another needle from the cartridge, remove the desired amount of dispersed and decontaminated cells from the receiver container 3, moves to a position relative to a series of sealed sample wells 2, sequentially punctures the seal on each of the well, deposits a predetermined amount of sample portion into each of the wells and removes the needle head. The needle head is disposed of in the disposal container 6.

Preferably, the wells 2 are prepackaged with various doses of various pharmaceutical agents to test the susceptibility of the tumor cells to each of the dosages and agents. Conditions for maintaining the wells should be close to physiological conditions. The pH of the medium in the wells should be close to physiological pH, preferably between pH 6-8, more preferably between about pH 7 to 7.8, with pH 7.4 being most preferred. Physiological temperatures range between about 30° C. and 40° C. Cells are preferably maintained at temperatures between about 35° C. and about 37° C. Similarly, cells may be cultured in levels of $O_2$ that are comparatively reduced relative to $O_2$ concentrations in air, such that the $O_2$ concentration is comparable to physiological levels (1-6%), rather than 20% $O_2$ in air. Given the short incubation times, it is not generally necessary to oxygenate the cells.

After incubation with the agents for a predetermined length of time, each well is treated with a fixative agent that fixes the cells and the indicator agent for later analysis. This treatment is accomplished with the operator member, a new needle head and a vial of fixative agent.

Solid tumor cells can also be cryopreserved until they are needed, by any method known in the art. The cells can be suspended in an isotonic solution, preferably a cell culture medium, containing a particular cryopreservant. Such cryopreservants include dimethyl sulfoxide (DMSO), glycerol and the like. These cryopreservants are used at a concentration of 5-15%, preferably 8-10%. Cells are frozen gradually to a temperature of −10° C. to −150° C., preferably −20° C. to −100° C., and more preferably −150° C.

It is clear, however, that modifications and/or additions can be made to the apparatus 10 and method as described heretofore, without departing from the field and scope of the present invention. For example, the counter container 46 and optical scanner 56 can be utilized on samples taken directly from the receiver container 14 prior to the operation of the process assembly 34.

Example 7

Dissaggregation Studies

MCF-7 human breast carcinoma cells (ATCC#HTB-22) are grown to 80% confluency in tissue culture then removed from the plates by gently scraping with a rubber policeman and suspended in growth medium. One aliquot of the cell suspension is passed through an 18 G needle twice (withdraw/infuse at 1 mL/s for each pass) resulting in a wall shear stress exposure of 172 dyne/cm² and a total exposure time for each cell or aggregate of 4 transits×14 msec/transit=56 msec. A second aliquot is passed through an 18 G needle five times (exposure time of 10 transits×14 msec/transit=140 msec). Representative samples from each are cytocentrifuged onto a glass slides, fixed with 95% ethanol and stained with the Papanicolaou stain. Photomicrographs of representative areas are obtained (Magnification ×200). For comparison, another image is obtained from an ultrasound-guided fine needle aspiration biopsy (FNA) of an enlarged lymph node found to contain metastatic breast cancer. Another image from this same human sample showed several groups of breast carcinoma cells in a background of numerous lymphocytes Scraped MCF-7 and processed MCF-7 with 2 withdraw/infuse cycles or 5 cycles through a 18 G needle (1") at 1 mL/sec. Note that 5 cycles of withdraw/infuse in sample C is sufficient to result in lysis and released nuclei, a condition that is not desired.

In the above experiment, an exposure of 2 cycles of withdrawal and infusion of MCF-7 cells represents a preliminary estimate of an operating condition, in the absence of EDTA, to disperse the scraped MCF-7 monolayer. This experimental condition provides an integrated shear exposure of $t_w(4_{transit})=172$ dyne/cm²×0.056 sec=9.6 dyne-sec/cm².

Example 8

Relative FOS Expression as Early Marker for Susceptibility to EGFR Blockers

At least 35 targeted cancer drugs aimed at the epidermal growth factor receptor (EGFR) are approved or in clinical trials. Unfortunately, biomarkers predicting tumor sensitivity to EGFR antagonists are unknown for most cancers. The variation in the expression of the early response gene FOS as a distal effect of EGFR inhibition can be evaluated and its relationship to antitumor effects the growth-inhibitory and FOS-modulating effects of gefitinib and erlotinib in human cancer cell lines (A431, CAL27, HN11, HuCCT1, and Hep2) determined. Next, these cell lines can be xenografted in mice and treated for 14 days with gefitinib (A431 and HuCCT1) or erlotinib (CAL27, HN11, and Hep2). Fine needle aspiration biopsy of tumors is done at baseline and after 14 days of therapy for FOS assessment. In addition, the feasibility of analyzing this marker in five paired tumor samples from a clinical trial of gefitinib in patients with solid tumors can be tested. In culture, gefitinib and erlotinib decrease FOS mRNA levels in the susceptible cell lines A431, CAL27, and HN11. Gefitinib or erlotinib abrogate the increase in FOS expression in vivo in EGFR-sensitive A431, CAL27, and HN11 tumors but not in resistant strains. In summary, variations in FOS expression reflect the pharmacologic actions of EGFR inhibitors with in vitro and in vivo models. See, e.g., Jimeno A, Kulesza P, Kincaid E, Bouaroud N, Chan A, Forastiere A, Brahmer J, Clark D P, Hidalgo M: C-fos Assessment as a Marker of Anti-Epidermal Growth Factor Receptor Effect, Cancer Res 2006, 66:2385-2390.

Example 9

Optimize Conditions for Rapid but Gentle Dispersion of FNAs

Selection of MCF-7 as Analog of Breast Tumor Cells in FNA

MCF-7 human breast cancer cells have been studied extensively as a model for hormone dependent breast cancer. The cells are a well-characterized estrogen receptor (ER) positive cell line and therefore are a useful in-vitro model of breast cancer research. The stable epithelial cell line is derived from primary culture of human breast carcinoma cells obtained from a pleural effusion from a female patient with metastatic disease (Soule, 1973). Since then the MCF7 cell line has arguably become the most widely investigated breast cancer model with thousands of citations as result of the comparable clinical attributes. Similar to hormone dependent ER-positive breast cancer, MCF7 cells are initially sensitive to anti-estrogens such as tamoxifen and fulvestrant. The MCF7 cell line has also served as the parental cell line for derivations of numerous other breast cancer models, which have repeatedly predicting clinical trial outcomes. Additionally, derivatives of the MCF7 cell line have provided insight into the mechanisms of resistance associated with first line hormonal therapy.

MCF-7 human breast carcinoma cells (ATCC#HTB-22) are grown in Modified Improved Minimum Essential medium (Invitrogen, Carlsbad, Calif.), 10% fetal bovine serum (Hyclone, Logan, Utah) and 1% penicillin/streptomycin solution (10,000 IU ea., Invitrogen). Upon 80% confluency cells are washed once with 10 mL of DPBS and removed from the flask by gentle scraping with a rubber cell scraper. Cells are suspended in 10 mL of growth medium and divided into replicate aliquots. This protocol has been validated to produce very large aggregates that are a surrogate of tumor cell clusters present in human breast cancer FNAs. The first aliquot (3 mL of suspended cells) is imaged and sized by image analysis and a coulter counter. After the initial size state of the first aliquot is counted, the sample is trypsinized and all cells counted.

Selection of HCT-116 Colon Carcinoma Cell Line as Analog of Metastatic Colon Carcinoma FNA The human colon carcinoma cell line HCT-116 (ATCC# CCL-247) is initially derived from a human male colon adenocarcinoma and has been widely utilized in subsequent studies. Its morphology resembles that of metastatic colon carcinoma and it has genetic features common to human colon carcinomas, including a mutation in codon 13 of the ras protooncogene. It is included in the NCI-60 panel of human cancer cell lines screened for pharmaceutical sensitivity. Extensive cDNA microarray gene expression data and correlative drug activity data are available on this cell line (http://discover.nci.nih.gov/).

HCT-116 Culture: HCT-116 cells are propagated in McCoy's 5a Modified Medium with 10% fetal bovine serum and incubated at 37 C plus 5% CO2. Medium is renewed every 2-3 days and cells are split when confluent at a subculture ratio of approximately 1:8 using a trypsin-EDTA solution.

FOS Staining Method: Cell clusters are fixed by incubating the slides in a solution containing 2% paraformaldehyde, 0.5% Triton X-100 at 4° C. for 15 minutes. The slides are then washed with 3% BSA, 0.5% Triton X-100 in PBS and incubated with 50 µl of sheep polyclonal antibody against FOS (Cambridge Research Inc., Wilmington, Del.) at a dilution of 1:20 (3% BSA, 0.5% Triton in PBS) for 2 hr. The slides are then washed three times with 5 ml of 3% BSA, 0.5% Triton in PBS solution. Each slide is incubated with 50 µl of fluorescein donkey antisheep IgG (H+ L) conjugate (Molecular Probes Inc., Eugene, Oreg.) (1:20 dilution) for 1 hr, washed 4 times with PBS, and imaged.

Trypan Blue Exclusion

This simple test measures the ability of cells to exclude dye if their membranes are intact. Depending on intensity, shear exposures can transiently permeabilize membranes or permanently damage the plasmalemma of cells. After dispersion experiments, cells will be suspended in Hank's balanced salt solution. A total of 0.2 mL of suspension is added to 0.8 mL of staining solution (0.5 mL of sterile Trypan blue solution 0.4% (Sigma T-8154) in 0.3 mL HBSS), incubated for 10 min, and 10 uL of the solution is counted with a hemacytometer to obtain cell number and % dead cells.

Live/Dead Staining

While trypan blue exclusion is simple and accurate, the use of fluorescent dyes is tested since a fluorescence determination of cell viability and cell number is more readily automated and miniaturized. Live/dead fluorescent staining uses two dyes: calcein AM and ethidium homodimer (EthD-1). Calcein AM is a non-fluorescent, cell permeable dye. It is cleaved to a fluorescent form in live cells by intracellular esterases. Ethidium homodimer (EthD-1) binds DNA and is a chromosome counter stain, but does not penetrate live cells and can be used to detect dead cells. Standard kits are available from ActiveMotif.

Detection of Apoptosis

Depending on the intensity of exposure, fluid shear forces can cause necrosis or apoptosis. To measure apoptosis in non-fixed cells at times of 0.5 to 1 hr after implementation of disaggregation protocols, cell permeable NucView-488 caspase 3 substrate available from Biotium, which takes advantage of the high DEVDase activity of caspase 3, is used. Caspase 3 is a common marker of apoptosis. NucView™ 488 caspase 3 substrate is a membrane permeable conjugate of a fluorogenic DNA dye and DEVD substrate. Cleavage of the dye by intracellular caspase 3 releases the DNA dye for simultaneous staining of the nucleus.

Determination of Fragmentation Rates from Experimental Data A genetic algorithm (GA) is used for the purpose of regressing size-dependent fragmentation kernels from a time series of experimentally measured size distributions at $t_1$, $t_2$, $t_3$, $t_4$, and $t_5$ obtained after each withdraw/infusion cycle of the experiment. The GA evolves an initial random population of kernel models in accordance with the principles of microevolution (crossover, random, fitness-mediated selection). After each transit through a syringe, a size distribution is measured at a discrete time into the fragmentation. For data obtained at a given average tube shear rate ($G_{avg}$), Equation 1 (a set of k ODEs) will be regressed by evaluation of the fitness of test "chromosomes" each containing an evolvable parameter set $[A(i,G_{avg}), y, g]$ for $a_i = A^*(G_{avg})^y (R_{hyd})^g$ for each cluster of i-cells. Note $A(i,G_{avg})$ is cell line and buffer-dependent.

Scraped monolayers of MCF-7 and HCT-116 are subjected to parabolic shear fields in sterile syringe needles (wall shear stress from 5 to 500 dyne/cm$^2$) for various times from 10 msec to 100 sec to evaluate dispersion characteristics. Extensional flows are tested via impinging flows with gap separations ranging from 100 microns to 1000 microns. Cells are tested for viability. Size distributions are obtained with a Coulter Counter. Cellular activation will be measured with FOS immunostaining, an early response gene that can be rapidly upregulated by high levels of shear forces. FOS induction results in intense nuclear staining and can be scored as % activation based on counting nuclei. Various buffers are tested including those containing chelators and viscosity modifiers and cell protectants, with the constraint of avoiding the use of proteases that destroy potentially important cell surface proteins.

FOS staining and viability in MCF-7 monolayers are assessed and compared to those obtained for the scraped monolayers (FNA analog) to establish baseline activation prior to shear disruption. To some extent, this mimics activation during FNA acquisition prior to dispersion. For each cell line, the most important parameters to determine are the minimum shear exposure strength (wall shear stress) and minimum shear exposure time (cumulative transit time through the needle) to disaggregate the sample. An aliquot (0.2 to 3 mL of suspension of scraped cells) will be passed through 15 to 21 G needles (0.5 to 2-in. long) at flow rates from 0.1 to 5 mL/s using a computer-controlled Harvard syringe pump 1 to 10 cycles. Each cycle (withdraw/infuse) of a 10 ml syringe is defined as one cycle. Needles are obtained from Popper & Sons (www.popperandsons.com), a custom manufacturer of components for automated liquid handling systems. Samples are imaged after each cycle. By use of different gauge needles and different needle lengths and different flow rates, the wall shear stress and cumulative exposure time can be varied independently. The wall shear stress scales linearly with flow rate Q but scales with the third power of the radius.

Exposures to laminar wall shear stresses of 10 to 150 dyne/cm$^2$ for times between 10 msec and 500 msec are generally sufficient to control the disaggregation state of the sample to obtain clusters of 5 to 10 cells/cluster. 2 to 4 cycles are generally optimum for reliable dispersion of the scraped samples. For FOS activation and cell viability studies, conditions and shear-induced FOS expression are monitored to disrupt scraped monolayers so that <15% of nuclei are positive for FOS expression.

Entry/Exit Effects

Experiments are conducted to evaluate the role of dispersal during sample entry into and exit out of the syringe (where substantial elongational flows can exist). Results are compared with the same gauge needle and same flow rate, but different needle lengths (0.5-in. versus 1.0-in. versus 2.0-in) and different cycle numbers such that samples can be generated that are exposed to the same wall shear stress and same cumulative shear exposure time, but different numbers of entry/exit events. Generally, sample entry and exit does not cause significant disaggregation.

For visual analysis of disaggregation after each cycle of withdrawal/infusion, samples are placed on ice for immediate cytocentrifugation. Cells will be prepared for microscopic analysis by first centrifuging each sample at 2000 rpm in a tabletop centrifuge (Hettich Rotina 46S) then resuspending the concentrated cell pellet in 500 µl of a balanced salt solution (Normosol). The cells will then be applied to a glass microscope slide using a cytocentrifuge at 750 rpm for 3 minutes (ThermoShandon Cytospin 4). The slides will be immediately fixed in 95% ethanol and stained with the Papanicolaou stain. Digital images of selected areas are obtained using an Adobe Photoshop (v. 5.5) and a light microscope (Olympus BX40) fitted with a digital camera (Kontron Elektronik Prog/Res/3012). Cells are subjected to particle counting image analysis (NIH Image) and results compared to cell counting obtained for the original aliquot.

Impinging Flow Systems

Impinging flows can be reliably obtained by directing the end of the needle toward a flat plate. Since the fluid jet exiting a submerged tube rapidly decays within a few tube diameters, it is important that the gap separation S be scaled with the needle gauge (Ga) such that S=k(Inner Diameter) are k=0.5 to 5. The gap separation is controlled with a manual micrometer. If large diameter needles are used, the wall shear stress drops rapidly (See Table 1). By directing small gauge needles (Ga=10 to 14) toward flat bottom wells and using lower flows (~0.1 mL/s) the tube wall shear stress can be maintained at <1 dyne/cm$^2$. In this configuration, disaggregation results by control of the impinging flow. Impinging flows allow cells to experience bursts of elongational shear forces for very short periods of time (microseconds). Impinging flows with aggregates may be more "nonlinear" in that the threshold for dispersal may be near the threshold. Tenacious structures (stromal tissue) in FNAs may require an impinging flow followed by standard tube flow. This can be easily achieved in an automated manner by use of a stepper motor to control needle position relative to the bottom of the container.

Cellular Activation Studies

After the first round of studies to determine fluidic conditions that disrupt cellular samples, the cell clusters are analyzed for membrane integrity (trypan blue staining and live/dead staining), cellular apoptosis (cell permeable caspase 3 fluorogenic assay), and cellular activation (FOS staining). As a positive control, conditions are already known for MCF-7 that cause loss of cell viability. Less than 5% of nuclei are FOS positive in scraped monolayers. Shear conditions to disrupt scraped monolayers to small clusters where FOS positive nuclei are <15%. For apoptosis studies, cells are allowed to incubate for 0.5 to 1 hr after dispersal to evaluate onset of apoptosis after dispersion.

Buffer Modifications

The dispersion buffer can be modified to enhance sample dispersion and minimize cellular activation. Chelation of extracellular calcium with EDTA facilitates disassembly of junctions holding cells together. EDTA exposure (5 mM, pH 7.4) followed by recalcification is tested as a cellular stimulant on its own. Reactive oxygen generation during dispersion of scraped monolayers may also result in cellular activation. N-acetyl-L-cysteine (NAC, 5 mM) may reduce FOS induction during cell dispersion. Finally, 0.2% (w/v) pluronic F68 is a polymer additive that has displayed cyto-protectant activity via cell membrane interactions in other membrane systems.

Example 10

Quantities of Cells

For HCT-116 and MCF-7 cells dispersed as in the previous examples using 400 dyne/cm2, nucleic acids were stabilized using Cell Protect. DNA and RNA were extracted using Qiagen extraction techniques. The number of cells necessary to obtain adequate RNA and DNA levels for analysis was determined. RNA from the cells was evaluated using RNA integrity evaluation (RIN), optical density 260/280, and total µg RNA. This experiment confirms, for example, that a sample size of greater than 100,000 cells is adequate for DNA and RNA analysis:

| Input | Output | | | | |
|---|---|---|---|---|---|
| | RNA | | | DNA | |
| Cell Number | RIN | 260/280 | ug | 260/280 | ug |
| 10,000 | 4.95 ± 1.77 | 1.19 ± 0.21 | 0.53 ± 0.06 | 11.71 ± 18.23 | 0.15 ± 0.42 |
| 100,000 | 5.80 ± 0.85 | 1.46 ± 0.10 | 1.08 ± 0.15 | 0.82 ± 2.62 | 0.39 ± 0.10 |
| 1,000,000 | 9.43 ± 0.64 | 1.98 ± 0.02 | 8.83 ± 3.78 | 2.15 ± 0.18 | 4.59 ± 1.07 |
| 10,000,000 | 9.97 ± 0.06 | 2.06 ± 0.01 | 41.73 ± 7.21 | 2.06 ± 0.05 | 17.41 ± 2.14 |

These results are also shown graphically in FIGS. 13 and 14.

Example 11

Cell Counting

For samples dispersed in the previous example (MCF-7 and HCT-116), cell counting is tested and validated with 10 to 100 µL cell suspension aliquots delivered to imaging chambers. Image counts are compared to both hemacytometer and Coulter counter scores. For the analysis of clumps, various imaging-processing algorithms is validated using samples that are divided into subsets for complete dispersion using trypsin and single cell counting. A Coulter counter can be used to get the size distribution through the use of a channelizer.

Nuclei Counting Protocol and Image Processing

The advantage of fluorescence staining of the nucleus is that nuclei are particularly large and discrete cellular objects that are easily identified in monolayer culture and suspension cells. In validating imaging methods for 1-step cell counting without separation or rinsing, dyes are tested that meet the following criteria: (1) can be applied to cells without the need of complex fix/wash/stain/wash protocols; (2) are easily excited at wavelengths available with low cost diodes or lasers; (3) produce a high signal-to-background ratio; and (3) produce a rapid stain of the cells, including membrane permeable SYTO-11 and SYTO-16 (Invitrogen). The uv-dyes (DAPI, Hoescht 33342) meet many of these criteria but require uv source, a disadvantage in Phase II when imaging systems must be miniaturized and economized. Cells are incubated in 10 mM SYTO11 (S7573, 508 nm EX/527 nm EM) or 10 uM SYTO-16 (S7578, 488 nm EX/527 nm EM) for up to 5 min prior to the imaging in chamber slides (Lab-Tek™ Chamber Slides™, Nunc; Culture area: 0.4 $cm^2$/well: working volume ul). Digital images are obtained using Adobe Photoshop (v. 5.5) and a microscope (Olympus) fitted with a digital camera (Kontron Elektronik Prog/Res/3012). Images are scored for nuclear counts by both visual inspection and image analysis software (NIH Image). These scores are compared to both hemacytometer and Coulter counter scores. The goal is to develop a fast and accurate nuclear counting protocol where 100 uL of the cellular suspension is added to 10 uL of staining solution and then imaged with blue excitation/green emission after 5 min incubation. Several variants are available in the SYTO series if the two chosen are inadequate. Similarly, the permeable nuclear stain CyTRAK Orange (Biostatus Ltd.; 488 nm EX/615 nm EM) can be tested for these applications.

The accurate counting of nuclei in small clusters is considerably more difficult than counting nuclei in cell monolayers or single cell suspensions. Edge detection and more complicated backgrounds may cause errors in the image analysis software. To ensure accuracy and consistency, comparison is made with cell counts obtained by full trysin/EDTA dispersion, to determine what inaccuracy exists as a function of mean cluster size, cluster size distribution, and cluster density/image area. If needed, size and intensity standards are added to the suspension for establishment of the signal range, background subtraction, thresholding, object detection, and particle counting.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents. Any headings used herein are provided solely for organizational purposes and are not intended to impart any division or meaning to this document, unless specifically indicated.

All documents cited herein, including websites, journal articles or abstracts, published or corresponding U.S. or foreign patent applications, issued or foreign patents, or any other documents, are each entirely incorporated by reference herein, including all data, tables, figures, and text presented in the cited document.

We claim:

1. A method for processing cancer cells from a solid tumor sample from a subject comprising the following steps in sequential order:
   (a) disaggregating and dispersing an aqueous solution containing live aggregated cancer cells into at least one test aliquot in a first isolated chamber, wherein a predetermined amount of laminar fluid shear force to disrupt aggregates of the cancer cells without killing the cancer cells and triggering only a minimal stress response or no stress response in the cancer cells is used;
   (b) optionally purifying the aliquot to increase the percentage of target cancer cells relative to other contaminating cell types by removing the contaminating cells;
   (c) distributing the optionally purified live cancer cells into one or more second isolated chambers for analysis;
   (d) contacting the distributed live cancer cells ex vivo with at least one agent to produce a measurable quantitatively or qualitative effect on a target ex vivo biomarker or biomolecules in a cellular pathway;
   (e) stabilizing the target ex vivo biomarker or biomolecule of the cancer cells within about one to four hours by lysing or fixing the cancer cells on a solid support using a solution comprising a polymer, thereby killing the cancer cells; and
   (f) measuring the changes in levels of the target ex vivo biomarker or biomolecule in the cellular pathway to assess the response of the target cancer cells to the at least one agent.

2. The method of claim 1, wherein the subject is a human and the method is performed at the point of care.

3. The method of claim 1, wherein the cancer cells are obtained from the subject as a solid tumor biopsy.

4. The method of claim 1, wherein the solid tumor sample is obtained using a fine needle aspiration technique.

5. The method of claim 1, in which the total number of the live aggregated cancer cells processed is between about 1000 and $10 \times 10^6$.

6. The method of claim 1, wherein the disaggregation step comprises passing the fluid comprising the cancer cells from the solid tumor sample through a needle or pipette tip of a predetermined size.

7. The method of claim 1, wherein the cancer cells are dispersed by the shear force of between about 100 to about 800 dyne/$cm^2$.

8. The method of claim 1, wherein the optional purification comprises immunodepletion.

9. The method of claim 1, wherein the one or more second isolated chambers contain less than about 1,000,000 of the purified cancer cells.

10. The method of claim 1, wherein the distribution step is done manually or using an automated system.

11. The method of claim 1, wherein the distributed live cancer cells have over about 75% viability as compared to the number of viable cancer cells in the fluid prior to the distribution.

12. The method of claim 1, wherein the distributed live cancer cells are divided into at least two aliquots and wherein each aliquot is contacted with a different at least one agent in step (d).

13. The method of claim 1, wherein the at least one agent is selected from the group consisting of a pharmaceutical agent, an agent for stimulating a cell, a polypeptide, a polynucleotide, an antibody, an Fab fragment, an Fc fragment, RNA, siRNA and a phosphoprotein.

14. The method of claim 1, wherein the cellular pathway is selected from the group consisting of a metabolic pathway, a replication pathway, a cellular signaling pathway, an oncogenic signaling pathway, an apoptotic pathway, and a pro-angiogenic pathway.

15. The method of claim 1, wherein the agent is an epidermal growth factor (EGF).

16. The method of claim 1, wherein the quantitative or qualitative effect measured is the expression level of a gene selected from the group consisting of an immediate or delayed early gene family.

17. The method of claim 1, wherein the target ex vivo biomarker or biomolecule is selected from the group consisting of ions, enzymes, lipids, and post-translationally modified proteins.

18. The method of claim 13, wherein the at least one agent is preloaded into one or more second isolated chambers before the purified live cancer cells are distributed into the one or more second isolated chambers.

19. The method of claim 1, wherein the at least one agent is a detectable agent selected from the group consisting of: an enzyme, fluorescent material, luminescent material, bioluminescent material, radioactive material, positron emitting metal using a positron emission tomography, and nonradioactive paramagnetic metal ion.

20. The method of claim 1, wherein the solid support is a glass slide.

* * * * *